(12) United States Patent
Buchberger et al.

(10) Patent No.: US 7,192,767 B2
(45) Date of Patent: Mar. 20, 2007

(54) MATRIX REACTOR AND A METHOD FOR PRODUCING PRODUCTS IN SAID REACTOR

(75) Inventors: Bernd Buchberger, Peissenberg (DE); Wolfgang Mutter, Bernried (DE); Albert Roeder, Muensing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 665 days.

(21) Appl. No.: 10/221,124

(22) PCT Filed: Mar. 7, 2001

(86) PCT No.: PCT/EP01/02548

§ 371 (c)(1),
(2), (4) Date: Jun. 4, 2003

(87) PCT Pub. No.: WO01/66243

PCT Pub. Date: Sep. 13, 2001

(65) Prior Publication Data

US 2004/0053405 A1 Mar. 18, 2004

(30) Foreign Application Priority Data

Mar. 8, 2000 (DE) ................................ 100 11 209

(51) Int. Cl.
*C12M 1/14* (2006.01)
*C12M 3/04* (2006.01)
*C12M 1/00* (2006.01)
*C12P 21/06* (2006.01)
*B01J 8/18* (2006.01)

(52) U.S. Cl. ................................ 435/299.1; 435/299.2; 435/289.1; 435/69.1; 435/283.1; 435/286.5; 435/41; 435/68.1; 422/139

(58) Field of Classification Search ............. 435/299.1, 435/299.2
See application file for complete search history.

(56) References Cited

U.S. PATENT DOCUMENTS 5,478,730 A     12/1995   Alakhov et al. ........... 435/68.1

(Continued)

FOREIGN PATENT DOCUMENTS

EP          0312617 A1      4/1989

(Continued)

OTHER PUBLICATIONS

Barker, P.E. et al., "Chromatographic Reactor Separator," Research Disclosure, May 1987, pp. 328.

(Continued)

*Primary Examiner*—Gladys J P Corcoran
*Assistant Examiner*—Nathan A. Bowers
(74) *Attorney, Agent, or Firm*—Marilyn L. Amick; Roche Diagnostics Operations, Inc.

(57) ABSTRACT

The present invention concerns a matrix reactor for reactions in which low-molecular and high-molecular reactants are involved wherein the reactor space $V_R$ contains a matrix and comprises a reaction compartment and a supply compartment, wherein the matrix is composed of a porous material which can take up low-molecular reactants and wherein the exclusion volume $V_0$ of the matrix is available as the reaction compartment and the matrix volume $V_M$ of the matrix is available as the supply compartment. The matrix reactor can be used for enzymatic processes, in particular for a coupled in vitro transcription/translation reaction to produce proteins.

11 Claims, 10 Drawing Sheets

U.S. PATENT DOCUMENTS

| | | | |
|---|---|---|---|
| 5,593,856 A | 1/1997 | Choi et al. | 435/68.1 |
| 5,851,907 A | 12/1998 | Mohan et al. | 436/518 |
| 6,033,868 A * | 3/2000 | Marszal et al. | 435/69.1 |
| 6,783,957 B1 * | 8/2004 | Biryukov et al. | 435/69.1 |
| 6,905,843 B1 * | 6/2005 | Endo et al. | 435/69.1 |

FOREIGN PATENT DOCUMENTS

| | | |
|---|---|---|
| EP | 0593757 A1 | 4/1994 |
| EP | 0695760 A1 | 2/1996 |
| JP | 7298893 | 11/1995 |
| JP | 1130395 | 5/1999 |
| WO | WO 95/17671 | 6/1995 |
| WO | WO 00/58493 | 10/2000 |

OTHER PUBLICATIONS

Baranov, Vladimir I. et al., "Gene Expression in Cell-Free System on Preparative Scale," Methods in Enzymology vol. 217, pp. 123-142(1993).

Chalfie, Martin et al., "Green Fluorescent Protein as a Marker for Gene Expression,," Science, vol. 263, Feb. 1994, pp. 802-805.

Crameri, Andreas et al., "Improved Green Fluorescent Protein by Molecular Evolution Using DNA Shuffling," Nature Biotechnology, vol. 14, Mar. 1996, pp. 315-319.

Spirin, Alexander S. et al., "Cell-Free Protein Synthesis Bioreactor," Frontiers in Bioprocessing II; American Chemical Society, p. 31-43, 1992.

* cited by examiner

Figure 1
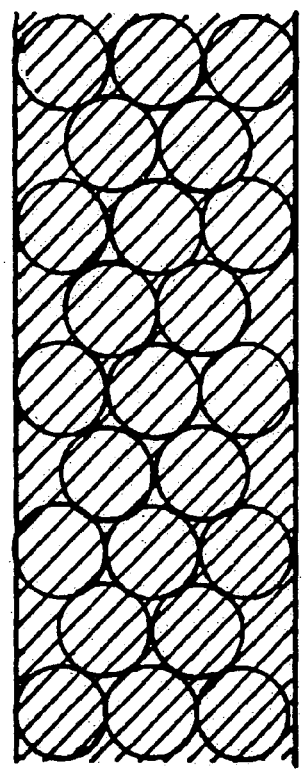 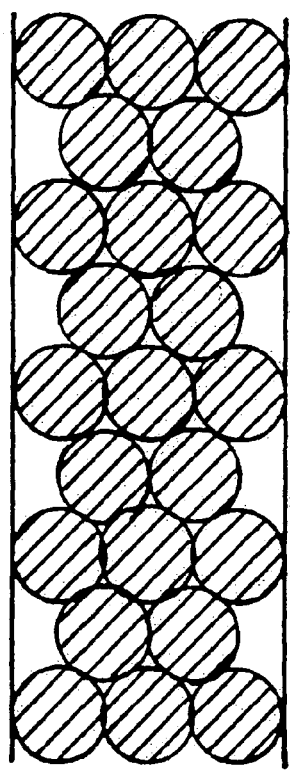 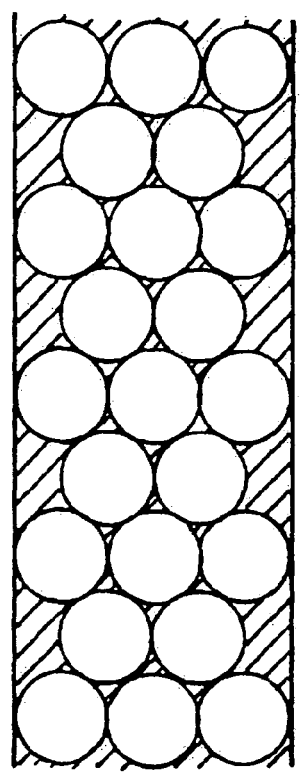
$V_R$ $V_M$ $V_O$

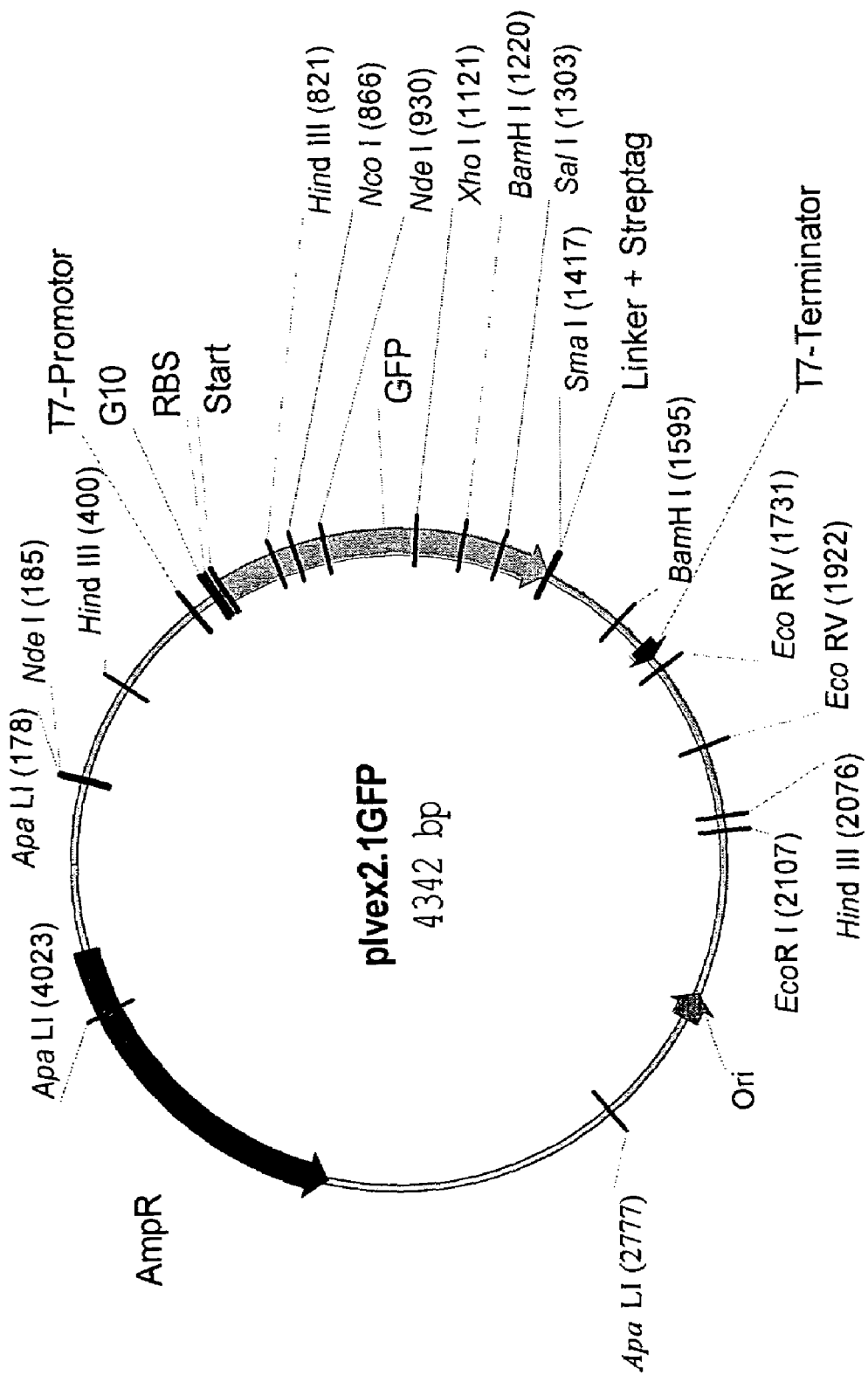
Figure 7/1

Figure 7/2

SEQ. ID. NO.: pIVEX 2.1-GFP aaacgacggccagtgccaagcttgcatgcaaggagatggcgcccaacagtcccccggccacggggcctgccaccatacccacgccgaa
acaagcgctcatgagcccgaagtggcgagcccgatcttccccatcggtgatgtcggcgatataggcgccagcaaccgcacctgtggcgcc
ggtgatgccggccacgatgcgtccggcgtagaggatcgagatctcgatcccgcgaaattaatacgactcactatagggagaccacaacggt
ttccctctagaaataattttgtttaactttaagaaggagatataccatgactagcaaaggagaagaacttttcactggagttgtcccaattcttgttg
aattagatggtgatgttaatgggcacaaattttctgtcagtggagagggtgaaggtgatgctacatacggaaagcttacccttaaatttatttgca
ctactggaaaactacctgttccatggccaacacttgtcactactttctcttatggtgttcaatgcttttcccgttatccggatcatatgaaacggcat
gacttttcaagagtgccatgcccgaaggttatgtacaggaacgcactatatctttcaaagatgacgggaactacaagacgcgtgctgaagtc
aagtttgaaggtgatacccttgttaatcgtatcgagttaaaaggtattgattttaaagaagatggaaacattctcggacacaaactcgagtacaac
tataactcacacaatgtatacatcacggcagacaaacaaaagaatggaatcaaagctaacttcaaaattcgccacaacattgaagatggatcc
gttcaactagcagaccattatcaacaaaatactccaattggcgatggccctgtccttttaccagacaaccattacctgtcgacacaatctgcccttt
tcgaaagatcccaacgaaaagagagaccacatggtccttcttgagtttgtaacagctgctgggattacacatggcatggatgaactatacaaa
cccgggagcgcttggagccacccgcagttcgaaaaataataagggcctcccactgactgctcttctgtcagtgggctactcctggactcggc
accagattgcctcatttttctcctctggcatttgtataaatccaccttgactggggaaattctcctggggtcaggtggcaccagcctggatccgg
ctgctaacaaagcccgaaaggaagctgagttggctgctgccaccgctgagcaataactagcataaccccttggggcctctaaacgggtcttg
aggggttttttgctgaaaggaggaactatatccggatatccacaggacgggtgtggtcgccatgatcgcgtagtcgatagtggctccaagtag
cgaagcgagcaggactgggcggcggccaaagcggtcggacagtgctccgagaacgggtgcgcatagaaattgcatcaacgcatatagcg
ctagcagcacgccatagtgactggcgatgctgtcggaatggacgatatcccgcaagaggcccggcagtaccggcataaccaagcctatgc
ctacagcatccagggtgacggtgccgaggatgacgatgagcgcattgttagatttcatacacggtgcctgactgcgttagcaatttaacttgtga
taaactaccgcattaaagcttatcgatgataagctgtcaaacatgagaattcgtaatcatggtcatagctgtttcctgtgtgaaattgttatccgctc
acaattccacacaacatacgagccggaagcataaagtgtaaagcctggggtgcctaatgagtgagctaactcacattaattgcgttgcgctca
ctgcccgctttccagtcgggaaacctgtcgtgccagctgcattaatgaatcggccaacgcgcggggagaggcggtttgcgtattgggcgctc
ttccgcttcctcgctcactgactcgctgcgctcggtcgttcggctgcggcgagcggtatcagctcactcaaaggcggtaatacggttatccaca
gaatcaggggataacgcaggaaagaacatgtgagcaaaaggccagcaaaaggccaggaaccgtaaaaaggccgcgttgctggcgttttc
cataggctccgcccccctgacgagcatcacaaaaatcgacgctcaagtcagaggtggcgaaacccgacaggactataaagataccaggc
gtttccccctggaagctccctcgtgcgctctcctgttccgaccctgccgcttaccggatacctgtccgcctttctcccttcgggaagcgtggcgc
tttctcatagctcacgctgtaggtatctcagttcggtgtaggtcgttcgctccaagctgggctgtgtgcacgaaccccccgttcagcccgaccg
ctgcgccttatccggtaactatcgtcttgagtccaacccggtaagacacgacttatcgccactggcagcagccactggtaacaggattagcag
agcgaggtatgtaggcggtgctacagagttcttgaagtggtggcctaactacggctacactagaaggacagtatttggtatctgcgctctgctg
aagccagttaccttcggaaaaagagttggtagctcttgatccggcaaacaaaccaccgctggtagcggtggtttttttgtttgcaagcagcaga
ttacgcgcagaaaaaaggatctcaagaagatcctttgatcttttctacggggtctgacgctcagtggaacgaaaactcacgttaagggattttg
gtcatgagattatcaaaaaggatcttcacctagatcctttaaattaaaaatgaagttttaaatcaatctaaagtatatatgagtaaacttggtctga
cagttaccaatgcttaatcagtgaggcacctatctcagcgatctgtctatttcgttcatccatagttgcctgactccccgtcgtgtagataactacg
atacgggagggcttaccatctggccccagtgctgcaatgataccgcgagacccacgctcaccggctccagatttatcagcaataaaccagc
cagccggaagggccgagcgcagaagtggtcctgcaactttatccgcctccatccagtctattaattgttgccgggaagctagagtaagtagtt
cgccagttaatagtttgcgcaacgttgttgccattgctacaggcatcgtggtgtcacgctcgtcgtttggtatggcttcattcagctccggttccca
acgatcaaggcgagttacatgatccccccatgttgtgcaaaaaagcggttagctccttcggtcctccgatcgttgtcagaagtaagttggccgca
gtgttatcactcatggttatggcagcactgcataattctcttactgtcatgccatccgtaagatgcttttctgtgactggtgagtactcaaccaagtc
attctgagaatagtgtatgcggcgaccgagttgctcttgcccggcgtcaatacgggataataccgcgccacatagcagaactttaaaagtgct
catcattggaaaacgttcttcggggcgaaaactctcaaggatcttaccgctgttgagatccagttcgatgtaacccactcgtgcacccaactga
tcttcagcatcttttactttcaccagcgtttctgggtgagcaaaaacaggaaggcaaaatgccgcaaaaaagggaataagggcgacacggaa
atgttgaatactcatactcttcctttttcaatattattgaagcatttatcagggttattgtctcatgagcggatacatatttgaatgtatttagaaaaata
aacaaataggggttccgcgcacatttccccgaaaagtgccacctgacgtctaagaaaccattattatcatgacattaacctataaaaataggcg
tatcacgaggccctttcgtctcgcgcgtttcggtgatgacggtgaaaacctctgacacatgcagctcccggagacggtcacagcttgtctgtaa
gcggatgccgggagcagacaagcccgtcagggcgcgtcagcgggtgttggcgggtgtcggggctggcttaactatgcggcatcagagca
gattgtactgagagtgcaccatatgcggtgtgaaataccgcacagatgcgtaaggagaaaataccgcatcaggcgccattcgccattcaggc
tgcgcaactgttgggaagggcgatcggtgcgggcctcttcgctattacgccagctggcgaaaggggggatgtgctgcaaggcgattaagttgg
gtaacgccagggttttcccagtcacgacgttgta

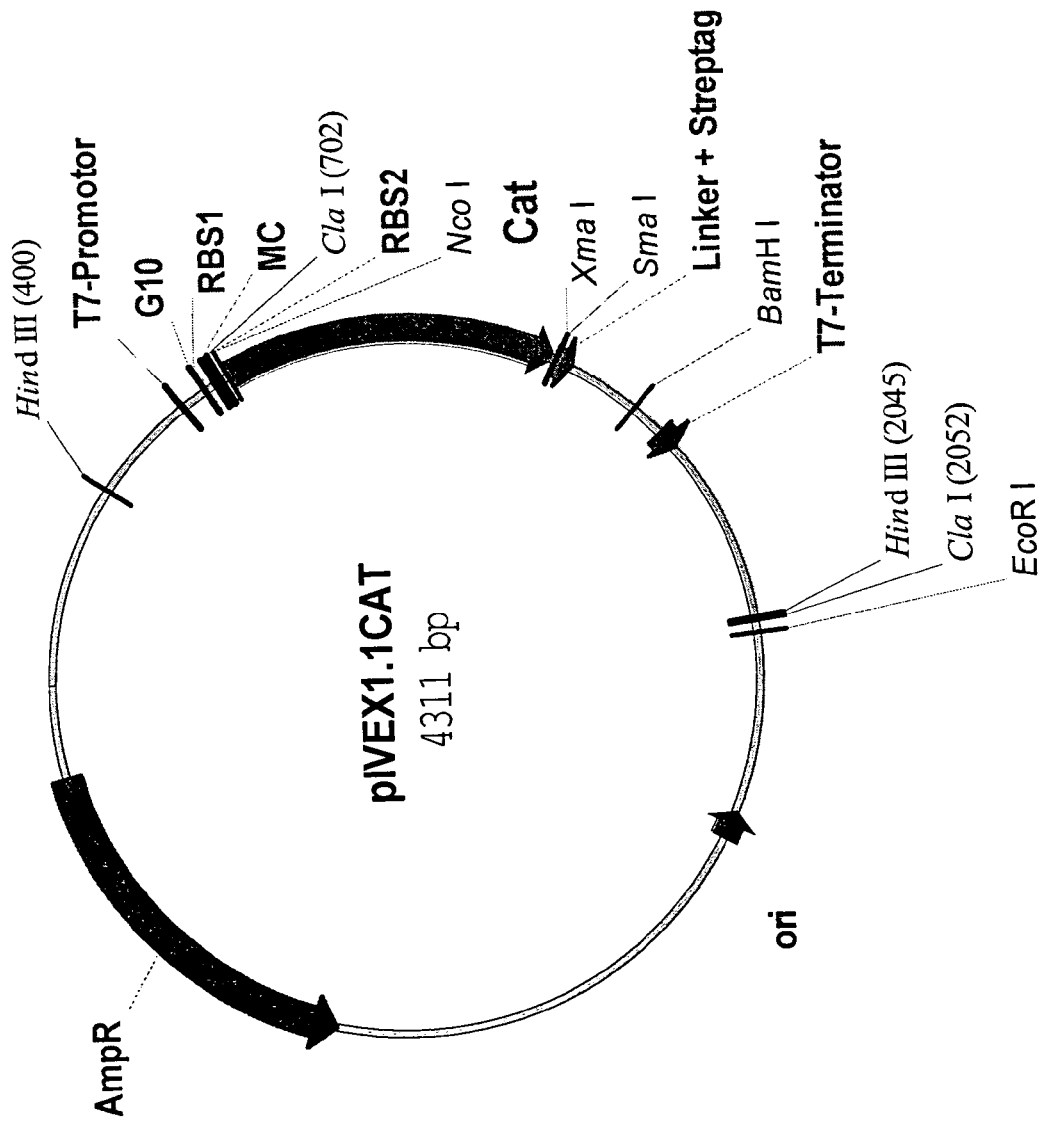
Figure 8/1

Figure 8/2

SEQ.ID.NO. 2: pIVEX 1.1-CAT tgtatcgattaaataaggaggaataaaccatggagaaaaaaatcactggatataccaccgttgatatatcccaatggcatcgtaaagaacattttgagg
catttcagtcagttgctcaatgtacctataaccagaccgttcagctggatattacggcctttttaaagaccgtaaagaaaaataagcacaagttttatccg
gcctttattcacattcttgcccgcctgatgaatgctcatccggaactccgtatggcaatgaaagacggtgagctggtgatatgggatagtgttcacccct
gttacaccgttttccatgagcaaactgaaacgttttcatcgctctggagtgaataccacgacgatttccggcagtttctacacatatattcgcaagatgtg
gcgtgttacggtgaaaacctggcctatttccctaaagggttattgagaatatgttttttcgtctcagccaatccctgggtgagtttcaccagttttgatttaa
acgtggccaatatggacaacttcttcgcccccgttttcacgatgggcaaatattatacgcaaggcgacaaggtgctgatgccgctggcgattcaggtt
catcatgccgtttgtgatggcttccatgtcggcagaatgcttaatgaattacaacagtactgcgatgagtggcagggcggggcgcccgggagcgctt
ggagccaccgcagttcgaaaaataataagggcctcccactgactgctcttctgtcagtgggctactcctggactcggcaccagattgcctcatttttc
tcctctggcattttgtataaatccaccttgactggggaaattctcctggggtcaggtggcaccagcctggatccggctgctaacaaagcccgaaagga
agctgagttggctgctgccaccgctgagcaataactagcataaccccttggggcctctaaacgggtcttgaggggttttttgctgaaaggaggaacta
tatccggatatccacaggacgggtgtggtcgccatgatcgcgtagtcgatagtggctccaagtagcgaagcgagcaggactgggcggcggccaa
agcggtcggacagtgctccgagaacgggtgcgcatagaaattgcatcaacgcatatagcgctagcagcacgccatagtgactggcgatgctgtcg
gaatggacgatatcccgcaagaggcccggcagtaccggcataaccaagcctatgcctacagcatccaggggtgacggtgccgaggatgacgatga
gcgcattgttagatttcatacacggtgcctgactgcgttagcaatttaactgtgataaactaccgcattaaagcttatcgatgataagctgtcaaacatga
gaattcgtaatcatggtcatagctgtttcctgtgtgaaattgttatccgctcacaattccacacaacatacgagccggaagcataaagtgtaaagcctgg
ggtgcctaatgagtgagctaactcacattaattgcgttgcgctcactgcccgctttccagtcgggaaacctgtcgtgccagctgcattaatgaatcggc
caacgcgcggggagaggcggtttgcgtattggcgctcttccgcttcctcgctcactgactcgctgcgctcggtcgttcggctgcggcgagcggtat
cagctcactcaaaggcggtaatacggttatccacagaatcaggggataacgcaggaaagaacatgtgagcaaaaggccagcaaaaggccagga
accgtaaaaaggccgcgttgctggcgtttttccataggctccgcccccctgacgagcatcacaaaaatcgacgctcaagtcagaggtggcgaaacc
cgacaggactataaagataccaggcgtttccccctggaagctccctcgtgcgctctcctgttccgaccctgccgcttaccggatacctgtccgcctttt
ctcccttcgggaagcgtggcgctttctcatagctcacgctgtaggtatctcagttcggtgtaggtcgttcgctccaagctgggctgtgtgcacgaaccc
cccgttcagcccgaccgctgcgccttatccggtaactatcgtcttgagtccaacccggtaagacacgacttatcgccactggcagcagccactggta
acaggattagcagagcgaggtatgtaggcggtgctacagagttcttgaagtggtggcctaactacggctacactagaaggacagtatttggtatctg
cgctctgctgaagccagttaccttcggaaaaagagttggtagctcttgatccggcaaacaaaccaccgctggtagcggtggtttttttgtttgcaagca
gcagattacgcgcagaaaaaaaggatctcaagaagatcctttgatcttttctacggggtctgacgctcagtggaacgaaaactcacgttaagggatttt
ggtcatgagattatcaaaaaggatcttcacctagatccttttaaattaaaaatgaagttttaaatcaatctaaagtatatatgagtaaacttggtctgacagt
taccaatgcttaatcagtgaggcacctatctcagcgatctgtctatttcgttcatccatagttgcctgactccccgtcgtgtagataactacgatacggga
gggcttaccatctggccccagtgctgcaatgataccgcgagacccacgctcaccggctccagatttatcagcaataaaccagccagccggaaggg
ccgagcgcagaagtggtcctgcaactttatccgcctccatccagtctattaattgttgccgggaagctagagtaagtagttcgccagttaatagtttgcg
caacgttgttgccattgctacaggcatcgtggtgtcacgctcgtcgtttggtatggcttcattcagctccggttcccaacgatcaaggcgagttacatga
tcccccatgttgtgcaaaaaagcggttagctccttcggtcctccgatcgttgtcagaagtaagttggccgcagtgttatcactcatggttatggcagcac
tgcataattctcttactgtcatgccatccgtaagatgcttttctgtgactggtgagtactcaaccaagtcattctgagaatagtgtatgcggcgaccgagtt
gctcttgcccggcgtcaatacgggataataccgcgccacatagcagaactttaaaagtgctcatcattggaaaacgttcttcggggcgaaaactctca
aggatcttaccgctgttgagatccagttcgatgtaacccactcgtgcacccaactgatcttcagcatcttttactttcaccagcgtttctgggtgagcaaa
aacaggaaggcaaaatgccgcaaaaaagggaataagggcgacacggaaatgttgaatactcatactcttcctttttcaatattattgaagcatttatca
gggttattgtctcatgagcggatacatatttgaatgtatttagaaaaataaacaaataggggttccgcgcacatttccccgaaaagtgccacctgacgt
ctaagaaaccattattatcatgacattaacctataaaaataggcgtatcacgaggccctttcgtctcgcgcgtttcggtgatgacggtgaaaacctctga
cacatgcagctcccggagacggtcacagcttgtctgtaagcggatgccgggagcagacaagcccgtcagggcgcgtcagcgggtgttggcgggt
gtcggggctggcttaactatgcggcatcagagcagattgtactgagagtgcaccatatgcggtgtgaaataccgcacagatgcgtaaggagaaaat
accgcatcaggcgccattcgccattcaggctgcgcaactgttgggaagggcgatcggtgcgggcctcttcgctattacgccagctggcgaaaggg
ggatgtgctgcaaggcgattaagttgggtaacgccagggttttcccagtcacgacgttgtaaaacgacggccagtgccaagcttgcatgcaaggag
atggcgcccaacagtccccggccacggggcctgccaccatacccacgccgaaacaagcgctcatgagcccgaagtggcgagcccgatcttcc
ccatcggtgatgtcggcgatataggcgccagcaaccgcacctgtggcgccggtgatgccggccacgatgcgtccggcgtagaggatcgagatct
cgatcccgcgaaattaatacgactcactataggggagaccacaacggtttccctctagaaataattttgtttaactttaagaggtatatattaa

MATRIX REACTOR AND A METHOD FOR PRODUCING PRODUCTS IN SAID REACTOR

The present invention concerns a matrix reactor for reactions in which low-molecular and high-molecular reactants are involved wherein the reactor space $V_R$ contains a matrix and comprises a reaction compartment and a supply compartment, wherein the matrix consists of a porous material which can take up low-molecular reactants and exclude high-molecular reactants and wherein the exclusion volume $V_0$ of the matrix is available as the reaction compartment and the matrix volume $V_M$ of the matrix is available as the supply compartment. The matrix reactor can be used for synthetic processes involving high-molecular catalysts (e.g. enzyme-catalysed reactions) and in particular for a coupled in vitro transcription/translation reaction to produce proteins.

An example of a reaction in which low-molecular and high-molecular reactants are involved is the in vitro transcription/translation reaction for the production of proteins. Reactors operating in a batch mode or using a process with a continuous supply and which are especially suitable for a coupled in vitro transcription/translation reaction for the production of proteins are already well known to a person skilled in the art (Baranov & Spirin (1993) Meth. Enzym. 217, 123–142). In a process for the coupled in vitro transcription/translation reaction for the production of proteins, a DNA-dependent RNA polymerase is used to synthesize the corresponding mRNA from a DNA template in a reaction mixture and the mRNA is then translated into protein by the ribosomal machinery. The reaction solution has a very complex composition. It contains low-molecular components (substrates, buffers, salts, activators, inhibitors, stabilizers) and high-molecular components (DNA template, RNA polymerase, ribosomes, tRNAs, enzymes, regulatory proteins). Some of the components are added in a purified form. Some of the important translation components (ribosomes, enzymes, regulatory proteins) are presently added to the system as cell extracts e.g. E. coli S30-lysate, reticulocyte lysate or wheat germ lysate. The yields of a coupled transcription/translation reaction have an order of magnitude of 1 mg/ml. A prerequisite for this is a continuous supply of substrates and energy components and the simultaneous separation or dilution of the end products of the reaction. In this manner it is possible to maintain the reaction for many hours. Such an experimental set-up has been implemented in the principles of continuous exchange cell-free (CECF) or continuous flow cell-free (CFCF) protein synthesis (U.S. Pat. No. 5,478,730; EPA 0 593 757; EPA 0 312 612; Baranov & Spirin (1993) Meth. Enzym. 217, 123–142). CECF reactors are composed of at least two discrete chambers which are separated from one another by porous membranes. This porous interface retains the high-molecular components in the reaction chamber while low-molecular components can be exchanged between the reaction chamber and supply chamber. In CFCF methods a supply solution is pumped directly into the reaction chamber and the end products of the reaction are pressed out of the reaction compartment through one or several ultrafiltration membranes.

However, all these reactors and the reactions that proceed therein have the following general disadvantages:

The reactors are composed of membrane surfaces and several chambers and are therefore complicated to manufacture.

If the batch size is changed (from a laboratory to a production scale), new reactors have to be designed, constructed and optimized.

The supply with substrates and the separation of the end products takes place through membranes. The construction imposes technical limitations on the available exchange surface since it is not possible to achieve surface/volume ratios of any size.

The membranes can easily become blocked which impairs the supply of the reaction.

The reaction solution and supply solution have to be continuously mixed (e.g. by stirring or pump circulation) to counteract gradients and undersupply.

A further problem with the reactors of the prior art is that in the case of a coupled in vitro transcription/translation reaction to produce proteins the lysates that are used are strongly diluted compared to the state in the E. coli cytosol. The reasons for this are 1. the lysis and preparation process for obtaining the lysate and 2. the dilution caused by the addition of all necessary components. This results in a reduced productivity since the equilibria of the macromolecular complexes are shifted to the dissociation side (law of mass action).

Several methods have already been described in the prior art to counteract this negative effect with the aim of increasing the active concentration of lysates. One method is to add high-molecular PEG (polyethylene glycol) to the reaction mixture which binds water and thus promotes the interaction of the remaining macromolecules (U.S. Pat. No. 5,593,856). A disadvantage of this method is that the reaction components and the accumulating product can aggregate and precipitate. Another method for concentrating lysates is to use the principle of reverse osmosis. In this method water is removed from the lysate through a semi-permeable surface (e.g. dialysis tube) by the action of a concentrated high-molecular solution of e.g. polyethylene glycol (Kigawa T. (1999) FEBS Lett. 442, 15–19). However, a disadvantage of this method is that it is too complicated. The latter also applies to the ultrafiltration method (U.S. Pat. No. 5,593,856) in which the lysate is concentrated before use by means of ultrafiltration. Also in this case an additional step is necessary to prepare the lysate.

The object of the present invention was to provide a reactor which is suitable for a coupled in vitro transcription/translation reaction for the production of proteins and which overcomes the disadvantages of the reactors of the prior art. In addition processes should be provided which are suitable for an in vitro transcription/translation reaction for the production of proteins and do not have the disadvantages of the prior art. In addition the process according to the invention should counteract a dilution of the macromolecular components. In particular it is intended to provide a reactor and a process which allows protein production by an in vitro transcription/translation reaction on a large scale.

The invention concerns a reactor for reactions in which low-molecular and high-molecular reactants are involved and in which the reactor space contains a matrix which comprises a reaction compartment and a supply compartment wherein the matrix consists of a porous material in which low-molecular reactants can largely diffuse freely, the high-molecular reactants cannot penetrate into the matrix, the low-molecular reactants cannot distribute within the entire reactor space $V_R$, the matrix volume $V_M$ is available as a supply compartment and the exclusion volume $V_0$ of the matrix is available as the reaction compartment.

In the reactor according to the invention the reaction compartment and supply compartment can be present in one reactor space as a result of the matrix structure of the reactor space. This variant is preferred. However it is also conceivable that the reaction compartment and supply compartment are present in one reaction space and that there is an additional supply reservoir which is connected directly to the reactor space or via a semi-permeable membrane.

Porous materials are used as the matrix and can be inorganic materials e.g. aluminium oxide and/or organic materials e.g. gels. The matrix must be weftable or capable of swelling in aqueous solution and have molecular sieve properties. According to the invention aqueous solution also refers to solutions that only contain 50% by volume water. In a preferred embodiment the matrix consists of polymers, cross-linked polymers (e.g. dextran), copolymers (e.g. polyacrylamide) or inorganic gels. A matrix is particularly preferred which comprises particles having a particle size in the range of 0.1 to 1000 µm. Matrices are preferred that have a low specific material density with reference to the form that is ready for use (i.e. hydrated). The specific material density is usually less than 0.5 g/ml, preferably less than 0.3 g/ml. The surface of the matrix particles (calculated as the surface of a sphere) is preferably in the range of 0.004 to 40 m$^2$/ml bed volume. The matrix is also defined by an exclusion limit (exclusion molecular weight) for macromolecules. The exclusion limit can be in the range of 0.5 to 300 kDa. An exclusion limit between 2 and 300 kDa is preferred and an exclusion limit between 10 and 100 kDa is particularly preferred. Suitable materials are commercially available (e.g. Sephadex®, Pharmacia; Bio-Gel®, BIO-RAD). It is possible to use a material with a uniform or different particle sizes. Mixtures of different materials can also be used. The matrix itself consists of an inert material which does not itself participate in the reaction, not even as catalyst. However, substances e.g. enzymes can be bound to this inert matrix as required.

The reactor space is completely or partially filled with this porous matrix material. A minimum filling of the reactor with matrix is necessary to achieve the inventive effect. The inventive effect can no longer be expected below 20 vol. % (bed volume). Of course in individual cases a matrix filling of for example 19.9% by volume should not be excluded. Hence, the reactor according to the invention is filled with at least ca. 20 vol % and particularly preferably with at least ca. 30 vol % of the porous matrix material. The variant in which the reactor is completely filled with porous matrix material is particularly preferred. A range of 80–100 vol % is extremely preferred.

The matrix divides the reactor volume into at least two compartments. One space that can only be occupied by low-molecular components and a space in which low-molecular as well as all high-molecular components reside. As a first approximation the resulting final concentrations of the reactants are determined by the sizes of the distribution spaces which they can reach.

The total reactor volume $V_R$ is occupied by the components having a molecular weight that is substantially below the exclusion limit of the matrix. This applies to substrates, buffer substances, salts and low-molecular inhibitors, activators or stabilizers. This also applies especially to low-molecular reaction end products which could potentially inhibit the reaction (e.g. product inhibition) or whose accumulation could change the general reaction conditions (e.g. pH value) and thus retard the reaction.

The high-molecular components cannot penetrate into the matrix. Their only distribution space is the volume between the particles of the matrix i.e. the exclusion volume $V_0$. This space is calculated from the total reactor volume minus the matrix volume ($V_0=V_R-V_M$) and equates with the reaction compartment. The reaction and supply compartments communicate with one another via short diffusion paths and via an extremely large exchange area. The volume ratio of the reaction compartment $V_0$ to the supply compartment $V_M$ depends on the nature, the size and the structural properties of the matrix and on the amount of matrix added. The ratio $V_R/V_M$ can be varied within a wide range.

The reaction volume for a particular fraction of macromolecules can be increased by mixing gel materials with different exclusion limits (e.g. 10 kDa and 200 kDa). Thus in this example the volume for ribosomes, DNA template and mRNA was minimized (molecular weight >200 kDa) whereas the loading of the tRNAs by aminoacyl-tRNA synthases (molecular weight <100 kDa) takes place in an expanded reaction space. This can be used to optimize the conditions for partial reactions.

The structure of the porous matrix also allows a specific modification of the surface or lumen. Enzymatic functions such as modified enzymes (restriction proteases) or an energy-regenerating enzyme system can be introduced into the system in a particular ratio immobilized on special particles. Chemical modification of the lumen would allow the specific adsorption of inhibitory substances.

The construction design of the matrix reactor allows a simple scale up from a laboratory into a production scale. In the simplest case commercial chromatography columns can be used as reactors which are available in sizes between 10 ml and 1000 liters. Once optimized the processes can be converted into a larger scale in a simple, quick and cost-effective manner. This considerably reduces the amount of planning, construction and evaluation of the reactors and production plants. The reactor material can vary from stainless steel to plastic or glass. However, other materials can also be used.

The reactor according to the invention differs from reactors that have been previously available by a very large exchange area between the supply compartment $V_M$ and reactor compartment $V_0$ and a substantially free diffusion of substrates between the two compartments, by extremely short diffusion paths between the supply compartment $V_M$ and reaction compartment $V_0$ which ensures an efficient supply to the reaction and eliminates the problem of gradient formation. It is not necessary to stir or mix.

by a simply construction and cost-effective manufacture.

by a simple transferability of the conditions optimized on a small scale to larger dimensions.

For the first time it is possible to exploit the special potentials of in vitro protein synthesis such as the production of toxic proteins or the incorporation of unnatural amino acids into proteins on a large scale and in an economic manner.

Potential embodiments of the reactor according to the invention are described in the following (see FIG. 1).

1) Matrix Column Reactor

The reactor consists of a chamber/column which is completely filled with matrix (total volume =$V_R$).

The supply compartment corresponds to the matrix volume ($V_M$).

The reaction compartment corresponds to the exclusion volume $V_0$ of the matrix.

The exclusion limit of the matrix is in the range of 0.5–300 kDa, preferably 2 to 300 kDa.

The reactor has an inlet (above) and outlet (below) for solutions.

The supply of solution results in a steady flow of the liquid column towards the outlet.

The reactor can be thermostatted.

Hence a matrix reactor is particularly preferred in which the matrix is a gel matrix. In particular a matrix reactor is preferred in which the reactor space has a cylindrical shape. Hence a preferred embodiment is a reactor in which the reactor is a chromatographic column filled with a gel matrix that can be thermostatted. In particular it is preferred that the matrix has an exclusion limit in the range of 2–300 kDa.

The reactor principle according to the invention can also be advantageously combined with established reactor types (batch, CECF, CFCF). This can lead to an improved yield due to increased productivity. Since smaller amounts of raw materials are required to reach the optimal concentration (e.g. DNA template, T7 polymerase, tRNAs), the inventive principle can also contribute to a cost reduction.

2) Matrix Batch Reactor

The reactor consists of a sealable reaction vessel.

The reactor has a sufficient volume to hold the reaction solution and a variable amount of gel matrix.

The reactor can be thermostatted (e.g. in a water bath).

3) CECF Reactor Containing a Matrix

The reactor is a CECF reactor comprising at least two chambers which are connected by one or several semipermeable membrane(s).

The reactor comprises at least one reaction chamber and at least one supply chamber.

The reaction chamber is partially or completely filled with a gel matrix.

The reactor can be thermostatted (e.g. incubator).

The reactor can optionally be stirred or shaken.

4) CFCF Reactor Containing a Matrix

The CFCF reactor comprises at least one chamber with an inlet opening and at least one porous surface.

This chamber is the reaction chamber and is partially or completely filled with matrix.

The supply solution can be pumped into the reaction chamber through the opening. The consumed supply solution is pressed out of the reaction chamber through an ultrafiltration membrane.

The reactor can be thermostatted (e.g. incubator).

The reaction solution can optionally be agitated by stirring, shaking or pump circulation.

An additional subject matter of the present invention is a process for producing products in the inventive reactor wherein the starting materials are low-molecular and high-molecular educts characterized in that the low-molecular components of the reaction mixture and in particular the substrates consumed by the reaction are distributed largely homogenFously in the entire reactor space $V_R$, only the exclusion volume of the matrix $V_0$ in the reactor space is available to the high-molecular components and in particular to the catalytically active reactants and the substrates can only be converted (reacted) in the exclusion volume of the matrix $V_0$.

The process according to the invention is preferably an enzymatic process in which one or several substrates are converted into one or several products by one or several enzymes. The reactor can in particular be used in processes for a coupled in vitro transcription/translation reaction to produce proteins.

The high-molecular components are ribosomes, tRNAs, DNA templates, RNA polymerases, mRNA and enzymes of intermediary metabolism (e.g. aminoacyl tRNA synthetases, transformylase, pyrophosphatase, nucleotide kinases) and the energy-regenerating system (e.g. acetate kinase, pyruvate kinase, creatine kinase, glycolytic enzymes, enzymes of the citrate cycle) and regulatory proteins (e.g. initiation factors, elongation factors, termination factors) and factors which support protein folding and carry out protein modifications.

The low-molecular components include substrates (the 20 naturally occurring amino acids, ATP, GTP, CTP, UTP, a secondary energy substrate such as e.g. acetyl phosphate) and effectors (buffer substance, salts, reducing compounds, folic acid, inhibitors, stabilizers). Low-molecular compounds are defined by the invention as being smaller than the exclusion limit of the matrix. Correspondingly high-molecular compounds are larger than the exclusion limit. Column processes are particularly preferred which are characterized in that the gel matrix is incorporated into the reactor space.

the gel matrix is equilibrated with the supply solution and is thermostatted at the reaction temperature (whereby the equilibration of the gel matrix can occur before or after the incorporation), the reaction solution is applied to the column, the reaction solution is stirred in the column for the duration of the reaction (static process) or is pumped slowly through the column (dynamic process) and after completion of the reaction the reaction solution containing the product is eluted from the column.

The inventive processes also include improvements to batch processes and processes with a continues supply.

Batch process: The addition of gel matrix equilibrated with supply solution to a batch reaction mixture allows the reaction period to be increased due to the improved substrate availability. As a first approximation adding the gel matrix results in no increase in volume for the high-molecular reactants and thus the reaction is not impaired by dilution effects. Overall the addition of matrix leads to an increased productivity with reference to the lysate.

CECF and CFCF processes: The presence of gel matrix in the reaction space leads overall to less dilution of the high-molecular reactants which increases the productivity with reference to the lysate. In this case the gel matrix equilibrated with supply solution is incorporated into the reaction chamber of a CECF or CFCF reactor, the reaction solution containing the high-molecular reactants is filled into the reaction chamber which starts the in vitro transcription/translation reaction to produce protein, in the case of the CECF process the supply chamber is filled with supply solution, in the case of the CFCF process the supply solution is pumped continuously into the reaction chamber, the reaction mixture is stirred or shaken for the duration of the reaction at a defined temperature and the reaction solution containing the product is removed from the reaction chamber at the end of the reaction.

The present invention also encompasses formulations for carrying out a coupled in vitro transcription/translation reaction to produce proteins. These formulations are especially suitable for producing proteins in the inventive matrix reactor. All the components required for the coupled in vitro transcription/translation to produce proteins are divided among two solutions i.e. the supply solution and reaction solution. The supply solution only contains low-molecular components such as buffers, salts, substrates and effectors. Suitable buffers and salts are e.g. Hepes or Tris, potassium ions, magnesium ions and ammonium ions. The required substrates are the 20 naturally occurring amino acids, the four ribonucleotides ATP, GTP, CTP, UTP or suitable metabolic precursors e.g. AMP, GMP, CMP, UMP and a secondary energy substrate such as phosphoenolpyruvate, creatine phosphate or acetyl phosphate or a suitable metabolic precursor of such substances. Effectors are substances which have a positive influence on the reaction or which suppress negative effects. These include one or several reducing compounds, in particular compounds containing thiol groups such as dithiothreitol, dithioerythrol, glutathione, mercaptoethane sulfonic acid, and additionally protein-stabilizing compounds such as glycerol, sugars, diethylene glycol, polyethylene glycol, detergents, co-factors as well as activators such as co-enzymes and co-substrates of intermediary metabolism e.g. folic acid, NAD/NADH, NADP/NADPH or precursors thereof, additionally inhibitors to suppress undesired side reactions such as rifampicin, Rnase inhibitors, protease inhibitors, azide.

The reaction solution contains the required high-molecular components and can also contain some or all of the low-molecular components of the supply solution. The basis of the reaction solution and source of many of the high-molecular components is a cell lysate. This lysate can be obtained from prokaryotic (e.g. E. coli) or from eukaryotic cells (e.g. yeast, reticulocytes, wheat embryos). Such lysates are usually obtained by cell lysis and separation of the particulate fraction (e.g. by centrifugation). These processes are well-known to a person skilled in the art from the literature. Lysates obtained in this manner can be added directly to the reaction solution or can be firstly processed and/or fractionated (e.g. by dialysis, precipitation, differential centrifugation, chromatographic methods, concentration steps) and added in the form of several suitable fractions.

The coupled in vitro transcription/translation reaction for producing proteins is extremely complex and requires a large number of cellular components. At present it is not possible to assume that the entirety of all these components is known or that their function is already fully understood.

High-molecular components which are introduced by the lysate are ribosomes, transfer RNAs, regulatory proteins and enzymes. The regulatory proteins are in particular initiation factors, elongation factors and termination factors of translation. Enzyme components are for example aminoacyl tRNA synthetases, enzyme systems for energy supply and conversion (e.g. acetate kinase, pyruvate kinase, creatine kinase, nucleoside diphosphate kinases, nucleoside monophosphate kinases, enzymes of glycolysis and of the citric acid cycle) and enzymes of intermediary metabolism such as pyrophosphatase, transformylase, transaminases. Furthermore it can be assumed that other components of the lysate are necessary for an efficient transcription and translation.

Other high-molecular substances are added to the reaction solution as individual components. These include transfer RNAs, DNA-dependent RNA polymerase preferably a viral polymerase such as T7-RNA polymerase, T3-RNA polymerase, SP6 RNA polymerase. Additionally enzymes to regenerate the energy components and enzymes of intermediary metabolism which are not contained in the lysate or not in an adequate quantity (e.g. creatine kinase, pyruvate kinase, pyrophosphatase). Additionally high-molecular inhibitors (e.g. RNasin). Additionally enzyme systems that are necessary for efficient and correct folding of proteins (e.g. chaperones, protein disulfide isomerase, peptidyl prolyl-cis-trans-isomerase). Additionally enzymes that are necessary for post-transcriptional modifications of proteins. Additionally macromolecular components which stabilize proteins or keep them in solution.

A circular (e.g. plasmid) or linear nucleic acid (e.g. PCR product) is added to the reaction solution as a template for the protein to be transcribed and translated. The code for the protein (e.g. a cDNA sequence) and in addition regulatory sequences which are required by the system for the correct transcription and translation are located on this template. These include for example a promoter sequence, ribosomal binding site, start codon, stop codon, polymerase termination sequence and translation enhancer. In addition the template can also contain regions that are necessary for cloning, amplification or mRNA stabilization.

In a preferred embodiment the supply solution has the following composition: 150–300 mM potassium acetate, 4–20 mM magnesium acetate, 1–10% glycerol, 0.5–2.5 mM ATP, 0.5–2.5 mM CTP, 0.5–2.5 mM GTP, 0.5–2.5 mM UTP, 0.1–2 mM of each amino acid (all 20 naturally occurring amino acids), 10.8 µg/ml folic acid, 0.5–5 mM EDTA, 100 mM HEPES-KOH pH 7.6/30° C., 1 µg/ml rifampicin, 0.03% sodium azide, 10–100 mM acetyl phosphate, 1–10 mM dithiothreitol, 1–10 mM mercaptoethane sulfonic acid, 70 mM KOH.

In a preferred embodiment the reaction solution has the following composition: 150–300 mM potassium acetate, 4–20 mM magnesium acetate, 1–10% glycerol, 0.5–2.5 mM ATP, 0.5–2.5 mM CTP, 0.5–2.5 mM GTP, 0.5–2.5 mM UTP, 0.1–2 mM of each amino acid (all 20 naturally occurring amino acids), 10.8 pg/ml folic acid, 0.5–5 mM EDTA, 100 mM HEPES-KOH pH 7.6/30° C., 1 µg/ml rifampicin, 0.03% sodium azide, 10–100 mM acetyl phosphate, 480 µg/ml tRNA from E. coli MRE600, 1–10 mM dithiothreitol, 1–10 mM mercaptoethane sulfonic acid, 70 mM KOH, 0.1 U/µl Rnase inhibitor, 1–20 µg/ml template, 100–500 µl/ml E. coli A19 lysate, 1–10 U/µl T7-RNA polymerase.

Thus the present invention also concerns the use of the inventive reactors for enzymatic reactions in particular for coupled in vitro transcription/translation reactions to produce proteins.

It is also conceivable that the reactor according to the invention could be used for reactions that proceed individually e.g. only the translation reaction to produce proteins or only the in vitro transcription reaction.

DESCRIPTION OF THE FIGURES

FIG. 1:
Possible embodiment of the matrix column reactor and the description of $V_R$ (reactor volume), $V_M$ (matrix volume) and $V_O$ (exclusion volume).

Figure 2:
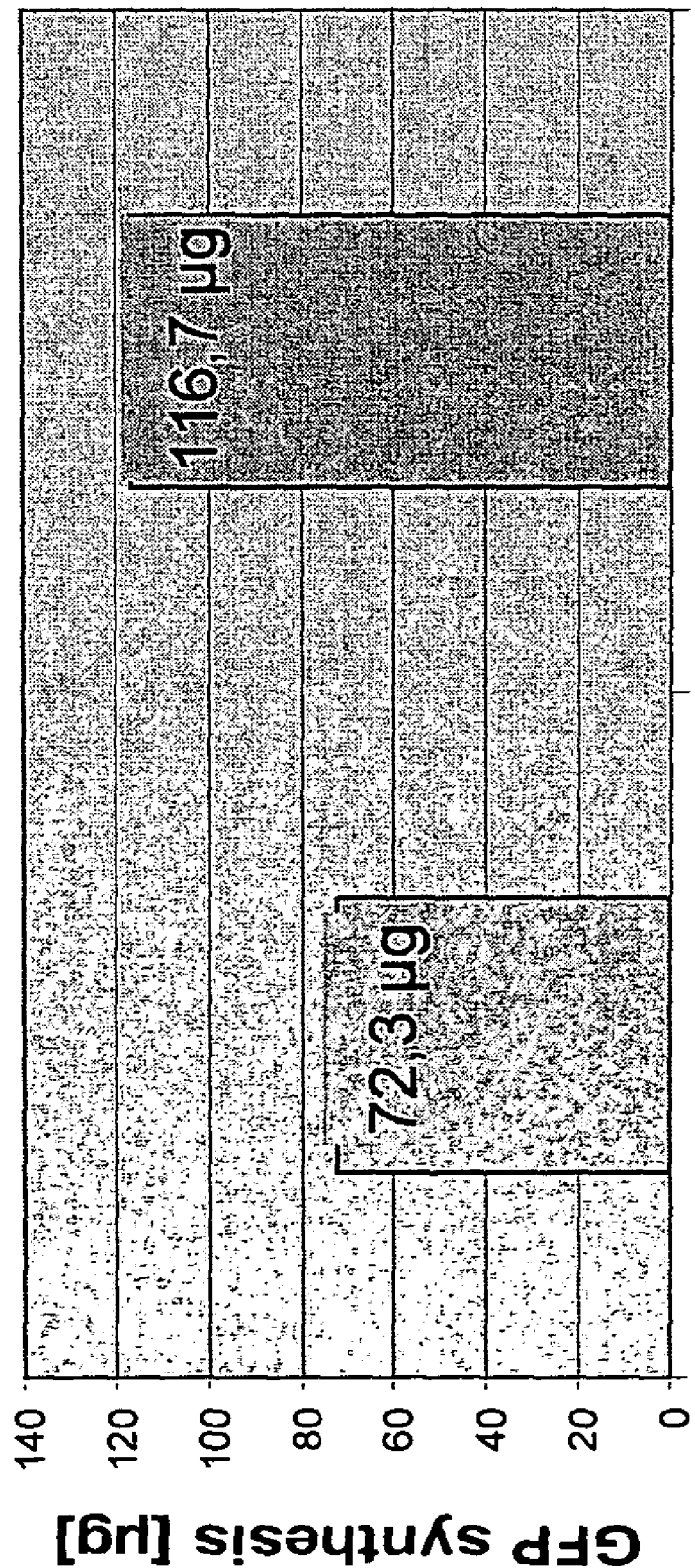
FIG. 2:
Synthesis of a GFP in a batch reaction with and without addition of equilibrated matrix (example 1).
Figure 3:
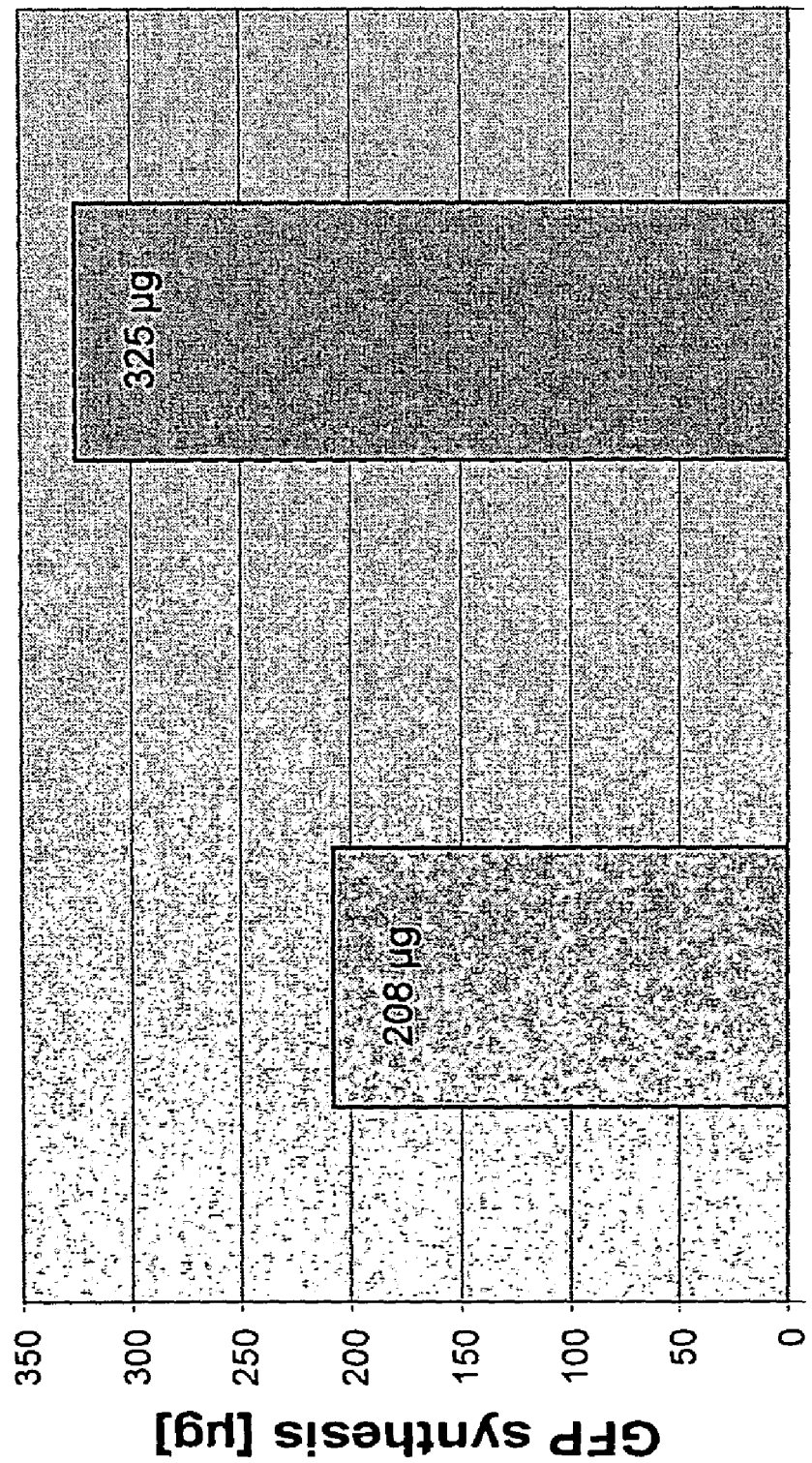
FIG. 3:
Synthesis of GFP in a CECF reactor and a CECF reactor containing matrix in the reaction chamber. Both reactions were carried out with the same reagents (example 2).
Figure 4:
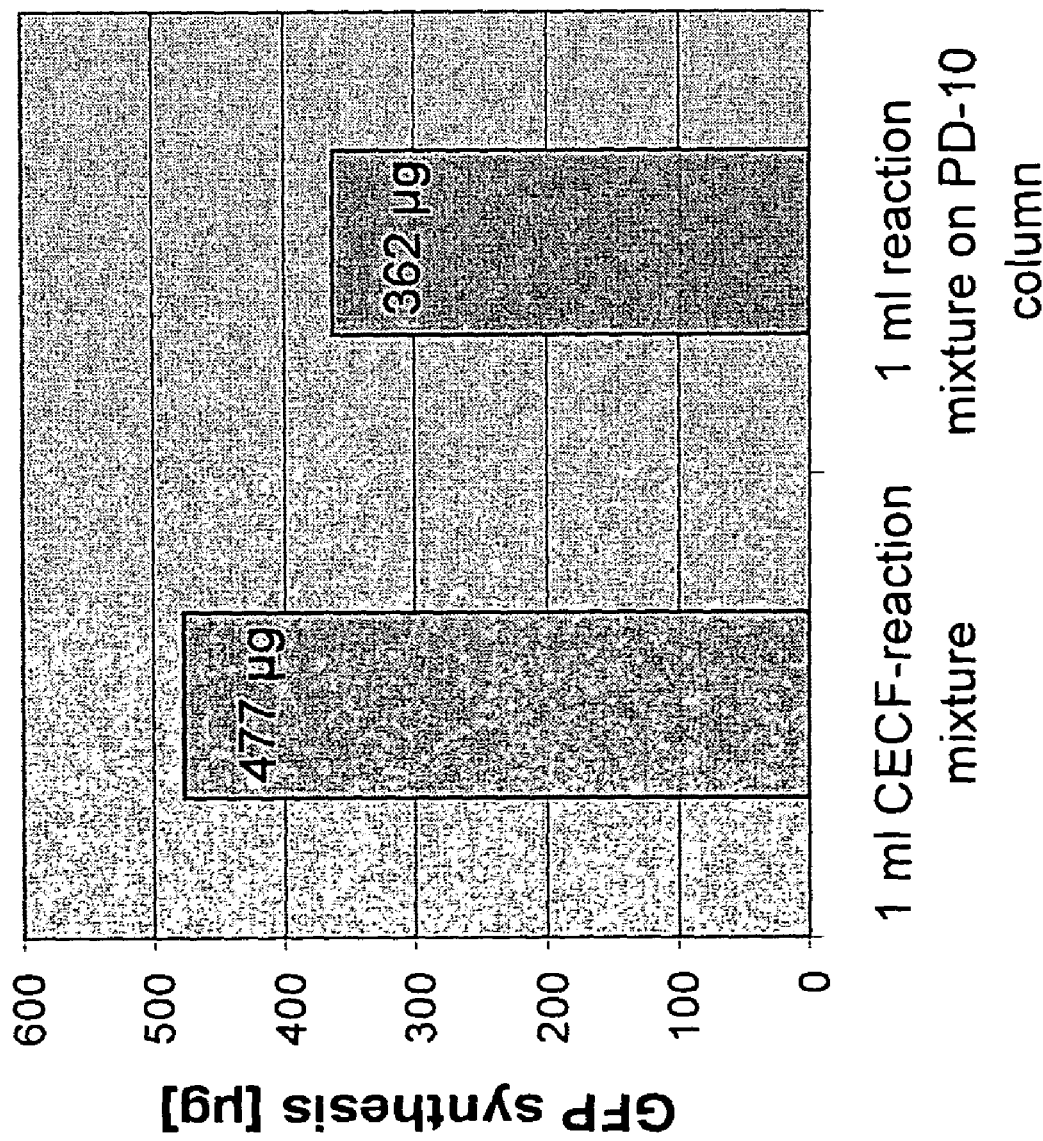
FIG. 4:
Synthesis of GFP in a CECF reactor and in a column reactor of comparable dimensions. Both reactions were carried out with the same reagents (example 3).
Figure 5:
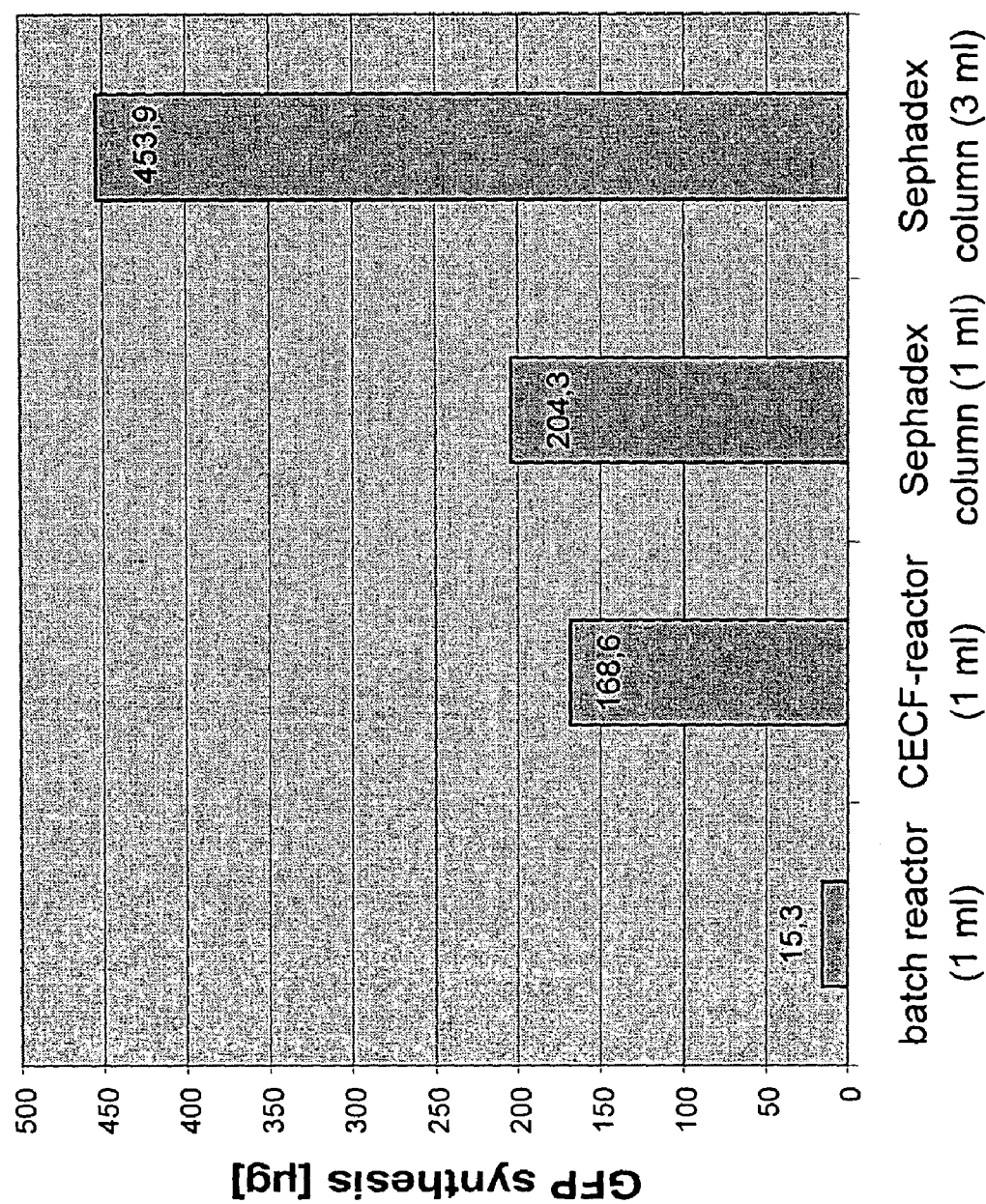
FIG. 5.
Figure 6:
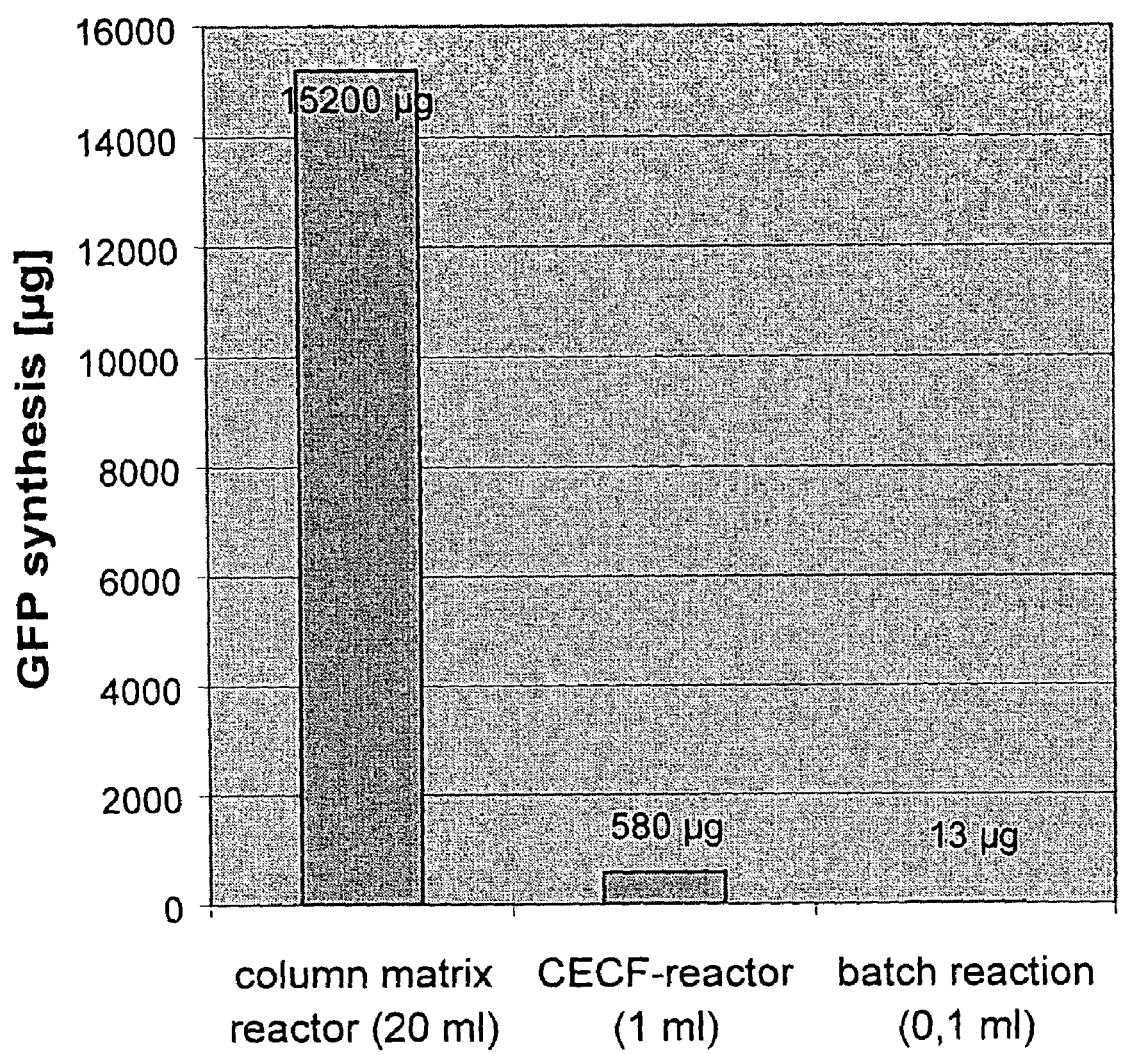

Synthesis of GFP in a CECF reactor and in column reactors (static process). The column reactors were loaded with 1 ml and 3 ml reaction solution. All reactions were carried out with the same reagents (example 4).

FIG. 6:

Synthesis of GFP in a 200 ml column reactor (dynamic process). 20 ml reaction solution was applied. A 0.1 ml batch reaction and a 1 ml CECF reaction were carried out using the same reagents as controls (example 5).

FIG. 7:

Plasmid map and sequence (SEQ ID NO: 1) of the GFP expression vector pIVEX2.1-GFP.

FIG. 8:

Plasmid map and sequence (SEQ ID NO: 2) of the CAT expression vector pIVEX 1.1-CAT.

EXAMPLES

The invention is further illustrated by the following examples. The listed reaction components, reactors and the GFP determination and CAT determination apply to all listed examples.

Cell-free protein synthesis of the green fluorescent protein (GFP) and chloramphenicol acetyltransferase (CAT) as examples is used to test the reactor according to the invention and the inventive process. Cell-free protein synthesis is carried out as a coupled transcription/translation reaction. The GFP-cDNA and CAT-cDNA is coded on an expression plasmid that is under the control of a T7 phage promoter. Transcription into mRNA takes place correspondingly by means of the DNA-dependent T7-RNA polymerase. The mRNA transcribed in vitro in this manner is translated into protein with the aid of the *E. coli* lysate that is present in the coupled system.

A) Reaction Components

1. Plasmids: pIVEX2.1-GFP contains the sequence for the green fluorescent protein from *Aequoria victori* in the form of a mutant GFPcycle3 (27 kDa) (Nature Biotechnology (1996) 14, 314–319); the coding region of the GFPcycle3 mutant was cloned into pTU58 instead of the wild type GFP sequence (Science (1994) 263, 802), (see FIG. 7/SEQ ID NO: 1). pIVEX 1.1-CAT contains the gene for chloramphenicol acetyl transferase from *E. coli* (see FIG. 8/SEQ ID NO: 2).

2. *E. coli* S30 lysate: The lysate was prepared using an *E. coli* A19 strain by a modified method according to Zubay (Annu. Rev. Genet. (1973) 7, 267). Modified lysate buffer: 100 mM HEPES-KOH pH 7.6/30° C., 14 mM magnesium acetate, 60 mM potassium acetate, 0.5 mM dithiothreitol. Differences in the yields in the various experiments are due to the different lysate preparations.

3. Reaction solution: 185 mM potassium acetate, 15 mM magnesium acetate, 4% glycerol, 2.06 mM ATP, 1.02 mM CTP, 1.64 mM GTP, 1.02 mM UTP, 257 μM of each amino acid (all 20 naturally occurring amino acids), 10.8 μg/ml folic acid, 1.03 mM EDTA, 100 mM HEPES-KOH pH 7.6/30° C., 1 μg/ml rifampicin, 0.03% sodium azide, 40 mM acetyl phosphate, 480 μg/ml tRNA from *E. coli* MRE600, 2 mM dithiothreitol, 10 mM mercaptoethane sulfonic acid, 70 mM KOH, 0.1 U/μl Rnase inhibitor, 15 μg/ml plasmid, 220 μl/ml *E. coli* A19 lysate, 2 U/μl T7-RNA polymerase.

4. Supply solution: 185 mM potassium acetate, 15 mM magnesium acetate, 4% glycerol, 2.06 mM ATP, 1.02 mM CTP, 1.64 mM GTP, 1.02 mM UTP, 257 μM of each amino acid (all 20 naturally occurring amino acids), 10.8 μg/ml folic acid, 1.03 mM EDTA, 100 mM HEPES-KOH pH 7.5/30° C., 1 μg/ml rifampicin, 0.03% sodium azide, 40 mM acetyl phosphate, 2 mM dithiothreitol, 10 mM mercaptoethane sulfonic acid, 70 mM KOH.

5. Equilibrated matrix: The gel matrices such as Sephadex G25 fine, were washed in a swollen state according to the manufacturer's instructions. Empty columns were packed by conventional methods for chromatographic columns. The packed chromatographic columns were equilibrated with 1–2 column volumes of supply solution. For batch and CECF reactions, the gel matrix was equilibrated by suspending it several times in the supply solution and sucked dry under a slight underpressure. The matrix treated in this manner was added to the batch mixture or incorporated into the CECF reactor.

B) Reactors

Sealable reaction vessels made of plastic were used for the batch reactions. The CECF reactors that were used comprise two chambers, the reaction chamber having a volume of 1 ml and the supply chamber having a volume of ca. 10 ml. The chambers are separated from one another by a 10 kDa dialysis membrane and can each be loaded through closable openings. Each chamber contains a magnetic stirrer bar. Ready-to-use PD10 columns (Pharmacia) or commercially available chromatographic columns (Pharmacia) that can be thermostatted and which were packed with gel matrix were used as matrix column reactors. All reactor types were operated at 30° C. Batch reaction mixtures were shaken, CECF reactions were stirred, matrix column reactors were loaded and eluted using pumps.

C) GFP Determination

GFP requires the presence of adequate amounts of oxygen in order to form the fluorophore. The amount of oxygen dissolved in the reaction solution is small and is not sufficient for complete conversion. Hence 11 samples were "matured" for 12 to 32 hours at 4° C. before the measurement. The samples were measured using a spectral fluorimeter from the Kontron Company, type Tegimenta SFM-25. The excitation was at a wavelength of 395 nm, the emission was determined at a wavelength of 510 nm.

Recombinant GFP from Roche Diagnostics, catalogue No. 1814524 was used as the standard. The calibration was carried out using standard solutions with concentrations of 1 μg/ml and 2 μg/ml.

For the measurement the samples were diluted 1:50 to 1:400 depending on the concentration with 100 mM HEPES-KOH pH 7.6/30° C., 14 mM magnesium acetate, 60 mM potassium acetate, 0.5 mM dithiothreitol.

D) CAT Determination

The CAT (chloramphenicol acetyltransferase) determination was carried out enzymatically using the CAT FAST green fluorescent substrate (molecular probes) according to the manufacturer's instructions.

E. Procedure

Example 1

Matrix Batch Reactor Versus Batch Reactor

The composition of the batch reaction mixture is described above (identical with the reaction solution). The template plasmid was added last to the mixture in order to start the reaction. 1 ml aliquots of the reaction solution were added to sealable reaction vessels. 2 g equilibrated gel matrix (Sephadex G25, fine) was added to one of the reaction mixtures. The mixtures were sealed and incubated for four hours at 30° C. while shaking. The yield of GFP was determined by a standard protocol (see above).

| Reaction mixture | GFP yield* |
|---|---|
| 1 ml batch reaction mixture | 72.3 µg |
| 1 ml batch reaction mixture + 2 g equilibrated matrix | 116.7 µg |

*maturation not required due to an adequate supply of oxygen

Result: Adding the gel matrix increases the yield of fluorescence-active GFP by 61% compared to the standard batch reaction.

Example 2

CECF Reactor Containing Matrix Versus CECF Reactor 0.5 ml equilibrated gel matrix (Sephadex G-10) was incorporated into the reaction chamber of a CECF reactor (1 ml reaction chamber, 10 ml supply chamber). 0.5 ml of a reaction solution with a modified composition was filled into the reaction chamber. The high-molecular components of the reaction solution were in double concentration (960 µg/ml tRNA from E. coli MRE600, 0.2 U/µl Rnase inhibitor, 30 µg/ml plasmid, 440 µl/ml E. coli A19 lysate, 4 U/µl T7-RNA polymerase) and the concentration of the low-molecular components were in single concentration (i.e. as in the supply solution). 10 ml supply solution was filled into the supply chamber. The comparative reaction in the CECF reactor was carried out under standard conditions. I.e. 1 ml reaction solution containing 15 µg GFP plasmid was filled into the reaction chamber and ca. 10 ml supply solution was filled into the supply chamber. Both reactors were incubated at 30° C. for 20 hours while stirring (150 rpm). At the end of each reaction period the content of the reaction chambers was removed and the yields of synthesized GFP were determined by a standard protocol (see above).

| Reaction mixture | GFP yield* |
|---|---|
| 1 ml CECF reaction mixture | 208 µg |
| 1 ml CECF reaction mixture containing matrix | 325 µg |

*36 h maturation at 4° C.

Result: The incorporation of matrix into the reaction chamber of the CECF reactor increased the production of fluorescence-active GFP by 56%.

Example 3

Comparison of Matrix Column Reactor (1/10 Dimension) Versus CECF Reactor

The CECF reaction was carried out under standard conditions i.e. 1 ml reaction solution containing 15 µg GFP plasmid was filled into the reaction chamber and ca. 10 ml supply solution was filled into the supply chamber. The reactor was incubated for 20 hours at 30° C. while stirring (150 rpm). A commercial PD-10 column filled with Sephadex G25 (Pharmacia) was used as the matrix column reactor. The reactor parameters were estimated on the basis of information from the manufacturer as follows: $V_R$=8.3 ml, $V_O$=2.5 ml, $V_M$=5.6 ml. The column was equilibrated with 10 ml supply solution. After adding 1 ml reaction solution (15 µg GFP plasmid/ml) the column was closed and incubated for 6 hours at 30° C. At the end of each reaction period the reaction solution was removed from the CECF reactor, or the reaction solution was eluted from the PD-10 column.

The yield of synthesized GFP was determined by the standard protocol (see above).

Result:

| Reaction mixture | GFP yield* |
|---|---|
| 1 ml CECF reaction mixture | 477 µg |
| 1 ml reaction mixture on PD-10 column | 362 µg |

*20 h GFP maturation at 4° C.

The reaction which was carried out in the PD-10 column yielded 362 µg fluorescence-active GFP. This results in a productivity of 76% compared to the CECF reaction in the same dimension (1 ml).

Example 4

Matrix Column Reactor (3/10 Dimension, Static Process)

10 ml Sephadex G25,fine was packed into two chromatographic columns and subsequently each was equilibrated with 1 column volume of supply solution. The reactor parameters were estimated as follows on the basis of the information from the manufacturer: $V_R$=10 ml, $V_O$=3 ml, $V_M$=7 ml. 1 ml reaction solution was applied to column 1 and 3 ml reaction solution was applied to column 2. Subsequently the columns were closed and incubated for 20 hours at 30° C. A 1 ml batch reaction and a 1 ml reaction in a CECF reactor were carried out as controls (also for 20 hours at 30° C.). After completion of the reaction period the columns were eluted. The yield of synthesized GFP in each was determined by a standard protocol (see above).

| Reaction mixture | reaction scale | GFP yield in µg/ml of reaction solution used | total GFP yield in µg |
|---|---|---|---|
| batch reaction | 1 ml | 15.3 µg/ml | 15.3 µg |
| CECF reactor | 1 ml | 168.6 µg/ml | 168.6 µg |
| matrix column reactor 1 | 1 ml | 204.3 µg/ml | 204.3 µg |
| matrix column reactor 2 | 3 ml | 151.3 µg/ml | 453.9 µg |

*20 h maturationat 4° C.

Result: The reaction yields of the two column reactor runs are comparable to the yields of the CECF reactor relative to the amount of reaction solution used. In the case of column 2 which was loaded with a three-fold amount of reaction solution, it was possible to increase the overall yield by 2.2-fold.

Example 5

Synthesis of GFP in a Matrix Column Reactor (20/200 Dimension, Dynamic Process)

Sephadex G25,fine was packed into a jacketed chromatography column (Pharmacia) and subsequently equilibrated with one column volume supply solution. The reactor parameters were estimated on the basis of information from the manufacturer as follows: $V_R$=200 ml, $V_0$=60 ml, $V_M$=140 ml. The column was thermostatted at 30° C. by means of a water bath. 20 ml reaction solution that was started with 151 µg/ml GFP plasmid was pumped onto the column (120 ml/h). Subsequently the reaction solution was pumped through the matrix at a rate of 12 ml/h. The eluate was fractionated at 4° C. A CECF reaction (1 ml dimension) and a batch reaction (0.1 ml dimension) were carried out as controls using the same reaction mixture. The yield of synthesized GFP in the fractions and in the control mixtures was determined by a standard protocol (see above).

| Reaction mixture | reaction scale | GFP yield in mg/ml of reaction solution used | total GFP yield in µg |
|---|---|---|---|
| matrix column reactor | 20 ml | 0.76 mg/ml | 15.2 mg |
| CECF reactor | 1 ml | 0.58 mg/ml | 0.58 mg |
| batch reaction | 0.1 ml | 0.13 mg/ml | 0.013 mg |

Result: 15.2 mg fluorescence-active GFP was produced within 10 hours in a matrix column reactor of 20 ml in size. Hence the yield was 0.76 mg/ml initial reaction solution. The yield in the CECF reactor of 0.58 mg/ml is in the range that is routinely obtained in this reactor type. Hence the matrix column reactor has a comparable productivity to the CECF reactor (131%). This experiment also shows that the dimensions can be increased by 20-fold without significant losses of yield compared to a 1 ml CECF mixture.

Example 6

CAT Synthesis in a Matrix Column Reactor (12.5/125 Dimension, Dynamic Process)

Sephadex G25,fine was packed into a jacketed chromatography column (Pharmacia) and subsequently equilibrated with one column volume supply solution (30 ml/h). The reactor parameters were estimated on the basis of information from the manufacturer as follows: $V_R$=125 ml, $V_M$=87.5 ml, $V_0$=37.5 ml. The column was thermostatted at 30° C. by means of a water bath. 12.5 ml reaction solution that was started with 15 µg/ml pIVEX 1.1-CAT plasmid was pumped onto the column (18 ml/h). Afterwards the reaction solution was pumped through the reactor at a rate of 3.6 ml/h. The eluate was fractionated at 4° C. The yield of functionally-active CAT was determined by means of an enzymatic fluorescence test.

| Reaction mixture | reaction scale | CAT yield in mg/ml of reaction solution used | total yield of CAT |
|---|---|---|---|
| matrix column reactor | 12.5 ml | 0.53 mg/ml | 6.6 mg |

Result: 6.6 mg CAT enzyme was produced in a 12.5 ml reaction mix in the matrix column reactor.

Example 7

CAT Synthesis in a Matrix Batch Reactor

Two 50 µl batch reactions were started with 15 µg/ml pIVEX 1.1-CAT. The reactions were firstly incubated at 30° C. After 30 minutes 100 mg equilibrated matrix (Sephadex G25,fine) was added to one batch. After 6 hours the yield of functionally-active CAT enzyme was determined by means of a fluorescence test.

| Reaction mixture | reaction scale | CAT yield in mg/ml of reaction solution used | total yield of CAT |
|---|---|---|---|
| batch reaction | 50 µl | 83 µg/ml | 4.2 µg |
| matrix batch reactor | 50 µl + 100 mg matrix | 154 µg/ml | 7.7 µg |

Result: The yield was increased by 74% by adding equilibrated matrix.

Example 8

Variation of the Amount of Matrix in the Matrix Batch Reactor

50 µl batch reactions were started with 15 µg/ml pIVEX 2.1-GFP. The reactions were incubated at 30° C. After 30 minutes various amounts (0 mg, 50 mg, 100 mg and 150 mg) of equilibrated matrix (Sephadex G25,fine) were added to the mixtures. After a reaction period of 5 hours the mixtures were kept at 4° C. to mature the GFP that was produced.

| Reaction mixture | reaction scale | GFP yield in mg/ml of reaction solution used | total yield of GFP* |
|---|---|---|---|
| batch reaction | 50 µl | 64 µg/ml | 3.2 µg |
| matrix batch reactor | 50 µl + 50 mg matrix | 111 µg/ml | 5.6 µg |
| matrix batch reactor | 50 µl + 100 mg matrix | 156 µg/ml | 7.8 µg |
| matrix batch reactor | 50 µl + 150 mg matrix | 160 µg/ml | 8 mg |

*1 h GFP maturation at 4° C.

Result: The yield was increased by up to 250% by adding equilibrated matrix.

Example 9

Comparison of Different Gel Materials in the Matrix Column Reactor (1/10 Dimension, Dynamic Process)

Various gel materials (Sephadex, Bio-Gel) were swelled according to the manufacturer's instructions, packed into 10 ml columns and equilibrated with 15 ml supply solution. 1 ml reaction solution (15 µg/ml pIVEX 2.1-GFP) was applied to each column. Directly afterwards the reaction solution was washed with 200 µl supply solution. 1 ml aliquots of supply solution were added at intervals of two hours (incubator, 30° C.). The eluted fractions were collected and stored at 4° C. The yield of synthesized GFP in each was determined by a standard protocol (see above).

| Gel material | reaction scale | GFP yield in µg/ml of reaction solution used | total yield of GFP* |
|---|---|---|---|
| Sephadex G25, medium | 1 ml | 126 µg/ml | 126 µg |
| Sephadex G50, fine | 1 ml | 121 µg/ml | 121 µg |
| Sephadex G75, fine | 1 ml | 30 µg/ml | 30 µg |
| Bio-Gel P6, medium | 1 ml | 180 µg/ml | 180 µg |
| Bio-Gel P10, medium | 1 ml | 251 µg/ml | 251 µg |
| Bio-Gel P30, medium | 1 ml | 201 µg/ml | 201 µg |

*20 h GFP maturation at 4° C.

Result: Various gel materials which differed with regard to the type of polymer, particle size and exclusion molecular weight can be used in the matrix reactor.

The invention claimed is:

1. A process for carrying out a coupled in vitro transcription and translation reaction to produce proteins, said method comprising the steps of:
   providing a reactor, said reactor comprising walls that define a total reactor volume $V_R$, a matrix comprising a porous material held within said total reactor volume, the matrix dividing the total reactor volume into a matrix volume $V_M$ and a matrix exclusion volume $V_0$, the division based on the size of the matrix pores and in the absence of a membrane separating the matrix volume $V_M$ and the matrix exclusion volume $V_0$, wherein at least 20 vol % of the total reactor volume is filled with said matrix,
   contacting said reactor with a supply solution, said supply solution comprising each of the 20 naturally occurring amino acids, ATP, GTP, CTP, and UTP, wherein said components of the supply solution have a molecular weight smaller than the pores of said matrix and are taken up into the matrix volume $V_M$ and are distributed largely homogeneously in the total reactor volume $V_R$,
   contacting said reactor with a reaction solution, said reaction solution comprising tRNAs, DNA templates, RNA polymerases, mRNA, and enzymes, wherein said tRNAs, DNA templates, RNA polymerases, mRNA, and enzymes each have a molecular weight larger than the pores of said matrix and are only localized in the matrix exclusion volume $V_0$,
   moving the reaction solution through the matrix exclusion volume $V_0$ while the reactor is thermostatted at a temperature conducive to in vitro transcription and translation, and
   obtaining said protein by recovering an eluate from the reactor.

2. The process as claimed in claim 1, wherein
   the matrix is first equilibrated with the supply solution, before
   the equilibrated matrix in the reactor volume is contacted with the reaction solution and wherein
   the reactor is maintained at a constant temperature.

3. The process as claimed in claim 2, wherein
   the reaction solution is applied to the column and
   the reaction solution is held in the column for the duration of the reaction.

4. The process as claimed in claim 2, wherein
   the reaction solution is applied to the column and
   additional reaction solution is pumped continuously or step-wise through the column for the duration of the reaction.

5. The process as claimed in claim 2, wherein
   the reactor is a batch reactor and
   the reaction solution and equilibrated matrix are brought together in the reactor volume,
   the added matrix volume being at least 20 vol % of the volume of the reactor volume.

6. The process as claimed in claim 2, wherein
   the reactor is a continuous exchange cell-free reactor having a reaction compartment,
   the matrix is incorporated into the reaction compartment of the continuous exchange cell-free reactor and
   the matrix volume is more than 20 vol % of the volume of the reaction compartment.

7. The process as claimed in claim 2, wherein
   the reactor is a continuous flow cell-free reactor having a reaction compartment,
   the matrix is incorporated into the reaction compartment of the continuous flow cell-free reactor and
   the matrix volume is more than 20 vol % of the volume of the reaction compartment.

8. The process of claim 2 wherein said matrix comprises particles having a particle size in the range of 0.1 to 1000 µm.

9. The process of claim 8 wherein said matrix has an exclusion limit selected from a range of about 10 to about 100 kDa.

10. The process of claim 9 wherein about 80 to about 100 vol % of the total reactor volume is filled with said matrix.

11. The process of claim 8 wherein said matrix comprises a mixture of particles having different exclusion ranges independently selected from the range of about 10 to about 100 kDa.

* * * * *

SEQUENCE LISTING

<160> NUMBER OF SEQ ID NOS: 2

<210> SEQ ID NO 1
<211> LENGTH: 4342
<212> TYPE: DNA
<213> ORGANISM: Green Fluorescent Protein Expression Vector pIVEX 2.1-GFP

<400> SEQUENCE: 1

```
aaacgacggc cagtgccaag cttgcatgca aggagatggc gcccaacagt cccccggcca      60
cggggcctgc caccataccc acgccgaaac aagcgctcat gagcccgaag tggcgagccc     120
gatcttcccc atcggtgatg tcggcgatat aggcgccagc aaccgcacct gtggcgccgg     180
tgatgccggc cacgatgcgt ccggcgtaga ggatcgagat ctcgatcccg cgaaattaat     240
acgactcact atagggagac cacaacggtt tccctctaga ataattttg tttaacttta     300 agaaggagat ataccatgac tagcaaagga gaagaacttt tcactggagt tgtcccaatt     360
cttgttgaat tagatggtga tgttaatggg cacaaatttt ctgtcagtgg agagggtgaa     420
ggtgatgcta catacggaaa gcttaccctt aaatttattt gcactactgg aaaactacct     480
gttccatggc caacacttgt cactactttc tcttatggtg ttcaatgctt ttcccgttat     540
ccggatcata tgaaacggca tgacttttc aagagtgcca tgcccgaagg ttatgtacag     600
gaacgcacta tatctttcaa agatgacggg aactacaaga cgcgtgctga agtcaagttt     660
gaaggtgata cccttgttaa tcgtatcgag ttaaaaggta ttgattttaa agaagatgga     720
aacattctcg gacacaaact cgagtacaac tataactcac acaatgtata catcacggca     780
gacaaacaaa agaatggaat caaagctaac ttcaaaattc gccacaacat tgaagatgga     840
tccgttcaac tagcagacca ttatcaacaa aatactccaa ttggcgatgg ccctgtcctt     900
ttaccagaca accattacct gtcgacacaa tctgcccttt cgaaagatcc caacgaaaag     960
agagaccaca tggtccttct tgagtttgta acagctgctg ggattacaca tggcatggat    1020
gaactataca aaccgggag cgcttggagc cacccgcagt cgaaaaaata ataagggcct    1080
cccactgact gctcttctgt cagtgggcta ctcctggact cggcaccaga ttgcctcatt    1140
tttctcctct ggcattttgt ataaatccac cttgactggg gaaattctcc tggggtcagg    1200
tggcaccagc ctggatccgg ctgctaacaa agcccgaaag gaagctgagt tggctgctgc    1260
caccgctgag caataactag cataacccct tggggcctct aaacgggtct tgaggggttt    1320
```

```
tttgctgaaa ggaggaacta tatccggata tccacaggac gggtgtggtc gccatgatcg   1380
cgtagtcgat agtggctcca agtagcgaag cgagcaggac tgggcggcgg ccaaagcggt   1440
cggacagtgc tccgagaacg ggtgcgcata gaaattgcat caacgcatat agcgctagca   1500
gcacgccata gtgactggcg atgctgtcgg aatggacgat atcccgcaag aggcccggca   1560
gtaccggcat aaccaagcct atgcctacag catccaggt gacggtgccg aggatgacga   1620
tgagcgcatt gttagatttc atacacggtg cctgactgcg ttagcaattt aactgtgata   1680
aactaccgca ttaaagctta tcgatgataa gctgtcaaac atgagaattc gtaatcatgg   1740
tcatagctgt ttcctgtgtg aaattgttat ccgctcacaa ttccacacaa catacgagcc   1800
ggaagcataa agtgtaaagc ctggggtgcc taatgagtga gctaactcac attaattgcg   1860
ttgcgctcac tgcccgcttt ccagtcggga acctgtcgt gccagctgca ttaatgaatc   1920
ggccaacgcg cggggagagg cggtttgcgt attgggcgct cttccgcttc ctcgctcact   1980
gactcgctgc gctcggtcgt tcggctgcgg cgagcggtat cagctcactc aaaggcggta   2040
atacggttat ccacagaatc aggggataac gcaggaaaga acatgtgagc aaaaggccag   2100
caaaaggcca ggaaccgtaa aaaggccgcg ttgctggcgt ttttccatag gctccgcccc   2160
cctgacgagc atcacaaaaa tcgacgctca agtcagaggt ggcgaaaccc gacaggacta   2220
taaagatacc aggcgtttcc ccctggaagc tccctcgtgc gctctcctgt tccgaccctg   2280
ccgcttaccg gatacctgtc cgcctttctc ccttcgggaa gcgtggcgct ttctcatagc   2340
tcacgctgta ggtatctcag ttcggtgtag tcgttcgct ccaagctggg ctgtgtgcac   2400
gaaccccccg ttcagcccga ccgctgcgcc ttatccggta actatcgtct gagtccaac   2460
ccggtaagac acgacttatc gccactggca gcagccactg gtaacaggat tagcagagcg   2520
aggtatgtag gcggtgctac agagttcttg aagtggtggc ctaactacgg ctacactaga   2580
aggacagtat ttggtatctg cgctctgctg aagccagtta ccttcggaaa aagagttggt   2640
agctcttgat ccggcaaaca aaccaccgct ggtagcggtg ttttttttgt ttgcaagcag   2700
cagattacgc gcagaaaaaa aggatctcaa gaagatcctt tgatcttttc tacgggtct   2760
gacgctcagt ggaacgaaaa ctcacgttaa gggattttgg tcatgagatt atcaaaaagg   2820
atcttcacct agatcctttt aaattaaaaa tgaagtttta aatcaatcta agtatatat   2880
gagtaaactt ggtctgacag ttaccaatgc ttaatcagtg aggcacctat ctcagcgatc   2940
tgtctatttc gttcatccat agttgcctga ctccccgtcg tgtagataac tacgatacgg   3000
gagggcttac catctggccc cagtgctgca atgataccgc gagacccacg ctcaccggct   3060
ccagatttat cagcaataaa ccagccagcc ggaagggccg agcgcagaag tggtcctgca   3120
actttatccg cctccatcca gtctattaat tgttgccggg aagctagagt aagtagttcg   3180
ccagttaata gtttgcgcaa cgttgttgcc attgctacag gcatcgtggt gtcacgctcg   3240
tcgtttggta tggcttcatt cagctccggt tcccaacgat caaggcgagt tacatgatcc   3300
cccatgttgt gcaaaaaagc ggttagctcc ttcggtcctc cgatcgttgt cagaagtaag   3360
ttggccgcag tgttatcact catggttatg gcagcactgc ataattctct tactgtcatg   3420
ccatccgtaa gatgcttttc tgtgactggt gagtactcaa ccaagtcatt ctgagaatag   3480
tgtatgcggc gaccgagttg ctcttgcccg gcgtcaatac gggataatac cgcgccacat   3540
agcagaactt taaaagtgct catcattgga aaacgttctt cggggcgaaa actctcaagg   3600
atcttaccgc tgttgagatc cagttcgatg taacccactc gtgcacccaa ctgatcttca   3660
```

-continued

```
gcatcttttta ctttcaccag cgtttctggg tgagcaaaaa caggaaggca aaatgccgca   3720
aaaaagggaa taagggcgac acggaaatgt tgaatactca tactcttcct ttttcaatat   3780
tattgaagca tttatcaggg ttattgtctc atgagcggat acatatttga atgtatttag   3840
aaaaataaac aaatagggt tccgcgcaca tttccccgaa aagtgccacc tgacgtctaa    3900
gaaaccatta ttatcatgac attaacctat aaaaataggc gtatcacgag gccctttcgt   3960
ctcgcgcgtt tcggtgatga cggtgaaaac ctctgacaca tgcagctccc ggagacggtc   4020
acagcttgtc tgtaagcgga tgccgggagc agacaagccc gtcagggcgc gtcagcgggt   4080
gttggcgggt gtcggggctg gcttaactat gcggcatcag agcagattgt actgagagtg   4140
caccatatgc ggtgtgaaat accgcacaga tgcgtaagga gaaaataccg catcaggcgc   4200
cattcgccat tcaggctgcg caactgttgg gaagggcgat cggtgcgggc ctcttcgcta   4260
ttacgccagc tggcgaaagg gggatgtgct gcaaggcgat taagttgggt aacgccaggg   4320
ttttcccagt cacgacgttg ta                                           4342
```

<210> SEQ ID NO 2
<211> LENGTH: 4311
<212> TYPE: DNA
<213> ORGANISM: Green Fluorescent Protein Expression Vector pIVEX 1.1-CAT

<400> SEQUENCE: 2

```
tgtatcgatt aaataaggag gaataaacca tggagaaaaa aatcactgga tataccaccg     60
ttgatatatc ccaatggcat cgtaaagaac attttgaggc atttcagtca gttgctcaat    120
gtacctataa ccagaccgtt cagctggata ttacggcctt tttaaagacc gtaaagaaaa    180
ataagcacaa gttttatccg gcctttattc acattcttgc ccgcctgatg aatgctcatc    240
cggaactccg tatggcaatg aaagacggtg agctggtgat atgggatagt gttcaccctt    300
gttacaccgt tttccatgag caaactgaaa cgttttcatc gctctggagt gaataccacg    360
acgatttccg gcagtttcta cacatatatt cgcaagatgt ggcgtgttac ggtgaaaacc    420
tggcctattt ccctaaaggg tttattgaga atatgttttt cgtctcagcc aatccctggg    480
tgagtttcac cagttttgat ttaaacgtgg ccaatatgga aacttcttc gccccccgttt   540 tcacgatggg caaatattat acgcaaggcg acaaggtgct gatgccgctg gcgattcagg    600
ttcatcatgc cgtttgtgat ggcttccatg tcggcagaat gcttaatgaa ttacaacagt    660
actgcgatga gtggcagggc ggggcgcccg ggagcgcttg gagccaccg cagttcgaaa    720 aataataagg gcctcccact gactgctctt ctgtcagtgg gctactcctg gactcggcac    780
cagattgcct cattttttctc ctctggcatt ttgtataaat ccaccttgac tggggaaatt   840 ctcctgggt caggtggcac cagcctggat ccggctgcta acaaagcccg aaaggaagct    900
gagttggctc tgccaccgc tgagcaataa ctagcataac cccttgggc ctctaaacgg     960 gtcttgaggg gttttttgct gaaaggagga actatatccg gatatccaca ggacgggtgt   1020
ggtcgccatg atcgcgtagt cgatagtggc tccaagtagc gaagcgagca ggactgggcg   1080
gcggccaaag cggtcggaca gtgctccgag aacgggtgcg catagaaatt gcatcaacgc   1140
atatagcgct agcagcacgc catagtgact ggcgatgctg tcggaatgga cgatatcccg   1200
caagaggccc ggcagtaccg gcataaccaa gcctatgcct acagcatcca gggtgacggt   1260
gccgaggatg acgatgagcg cattgttaga tttcatacac ggtgcctgac tgcgttagca   1320
atttaactgt gataaactac cgcattaaag cttatcgatg ataagctgtc aaacatgaga   1380
```

-continued

```
attcgtaatc atggtcatag ctgtttcctg tgtgaaattg ttatccgctc acaattccac    1440
acaacatacg agccggaagc ataaagtgta agcctggggg tgcctaatga gtgagctaac    1500
tcacattaat tgcgttgcgc tcactgcccg ctttccagtc gggaaacctg tcgtgccagc    1560
tgcattaatg aatcggccaa cgcgcgggga gaggcggttt gcgtattggg cgctcttccg    1620
cttcctcgct cactgactcg ctgcgctcgg tcgttcggct gcggcgagcg gtatcagctc    1680
actcaaaggc ggtaatacgg ttatccacag aatcagggga taacgcagga agaacatgt    1740 gagcaaaagg ccagcaaaag gccaggaacc gtaaaaaggc cgcgttgctg gcgttttcc    1800 ataggctccg ccccctgac gagcatcaca aaaatcgacg ctcaagtcag aggtggcgaa    1860
acccgacagg actataaaga taccaggcgt ttccccctgg aagctccctc gtgcgctctc    1920
ctgttccgac cctgccgctt accggatacc tgtccgcctt tctcccttcg ggaagcgtgg    1980
cgctttctca tagctcacgc tgtaggtatc tcagttcggt gtaggtcgtt cgctccaagc    2040
tgggctgtgt gcacgaaccc cccgttcagc ccgaccgctg cgccttatcc ggtaactatc    2100
gtcttgagtc caacccggta agacacgact tatcgccact ggcagcagcc actggtaaca    2160
ggattagcag agcgaggtat gtaggcggtg ctacagagtt cttgaagtgg tggcctaact    2220
acggctacac tagaaggaca gtatttggta tctgcgctct gctgaagcca gttaccttcg    2280
gaaaaagagt tggtagctct tgatccggca aacaaaccac cgctggtagc ggtggttttt    2340
ttgtttgcaa gcagcagatt acgcgcagaa aaaaggatc tcaagaagat cctttgatct    2400
tttctacggg gtctgacgct cagtggaacg aaaactcacg ttaagggatt ttggtcatga    2460
gattatcaaa aaggatcttc acctagatcc ttttaaatta aaaatgaagt tttaaatcaa    2520
tctaaagtat atatgagtaa acttggtctg acagttacca atgcttaatc agtgaggcac    2580
ctatctcagc gatctgtcta tttcgttcat ccatagttgc ctgactcccc gtcgtgtaga    2640
taactacgat acgggagggc ttaccatctg gccccagtgc tgcaatgata ccgcgagacc    2700
cacgctcacc ggctccagat ttatcagcaa taaaccagcc agccggaagg gccgagcgca    2760
gaagtggtcc tgcaacttta tccgcctcca tccagtctat taattgttgc cgggaagcta    2820
gagtaagtag ttcgccagtt aatagtttgc gcaacgttgt tgccattgct acaggcatcg    2880
tggtgtcacg ctcgtcgttt ggtatggctt cattcagctc cggttcccaa cgatcaaggc    2940
gagttacatg atcccccatg ttgtgcaaaa aagcggttag ctccttcggt cctccgatcg    3000
ttgtcagaag taagttggcc gcagtgttat cactcatggt tatggcagca ctgcataatt    3060
ctcttactgt catgccatcc gtaagatgct tttctgtgac tggtgagtac tcaaccaagt    3120
cattctgaga atagtgtatg cggcgaccga gttgctcttg cccggcgtca tacgggata     3180 ataccgcgcc acatagcaga actttaaaag tgctcatcat tggaaaacgt tcttcggggc    3240
gaaaactctc aaggatctta ccgctgttga tccagttc gatgtaaccc actcgtgcac      3300
ccaactgatc ttcagcatct tttactttca ccagcgtttc tgggtgagca aaaacaggaa    3360
ggcaaaatgc cgcaaaaaag ggaataaggg cgacacggaa atgttgaata ctcatactct    3420 tccttttca atattattga agcatttatc agggttattg tctcatgagc ggatacatat     3480
ttgaatgtat ttagaaaaat aaacaaatag gggttccgcg cacatttccc cgaaaagtgc    3540
cacctgacgt ctaagaaacc attattatca tgacattaac ctataaaaat aggcgtatca    3600
cgaggccctt tcgtctcgcg cgtttcggtg atgacggtga aaacctctga cacatgcagc    3660
tcccggagac ggtcacagct tgtctgtaag cggatgccgg gagcagacaa gcccgtcagg    3720
gcgcgtcagc gggtgttggc gggtgtcggg gctggcttaa ctatgcggca tcagagcaga    3780
```

```
ttgtactgag agtgcaccat atgcggtgtg aaataccgca cagatgcgta aggagaaaat    3840
accgcatcag gcgccattcg ccattcaggc tgcgcaactg ttgggaaggg cgatcggtgc    3900
gggcctcttc gctattacgc cagctggcga aaggggatg tgctgcaagg cgattaagtt    3960
gggtaacgcc agggttttcc cagtcacgac gttgtaaaac gacggccagt gccaagcttg    4020
catgcaagga gatggcgccc aacagtcccc cggccacggg gcctgccacc atacccacgc    4080
cgaaacaagc gctcatgagc ccgaagtggc gagcccgatc ttccccatcg gtgatgtcgg    4140
cgatataggc gccagcaacc gcacctgtgg cgccggtgat gccggccacg atgcgtccgg    4200
cgtagaggat cgagatctcg atcccgcgaa attaatacga ctcactatag ggagaccaca    4260
acggtttccc tctagaaata attttgttta actttaagag gtatatatta a             4311
```